United States Patent [19]
Cornelissen et al.

[11] Patent Number: 5,877,306
[45] Date of Patent: Mar. 2, 1999

[54] **MODIFIED *BACILLUS THURINGIENSIS* INSECTICIDAL-CRYSTAL PROTEIN GENES AND THEIR EXPRESSION IN PLANT CELLS**

[75] Inventors: Marc Cornelissen, Heusden; Piet Soetaert, Laarne, both of Belgium; Maike Stam, Amstelveen, Netherlands; Jan Dockx, Ghent, Belgium

[73] Assignee: Plant Genetic Systems, N.V., Ghent, Belgium

[21] Appl. No.: 694,824

[22] Filed: Aug. 9, 1996

Related U.S. Application Data

[62] Division of Ser. No. 453,104, May 30, 1995, Pat. No. 5,633,446, which is a continuation of Ser. No. 937,869, filed as PCT/EP91/00733 Apr. 17, 1991, abandoned.

[30] Foreign Application Priority Data

Apr. 18, 1990 [GB] United Kingdom .................. 90401055

[51] Int. Cl.⁶ .............................. C12N 5/14; C12N 15/32; C12N 15/82
[52] U.S. Cl. .................................... 536/23.71; 435/172.3; 435/419; 435/418
[58] Field of Search .............................. 435/252.5, 172.3, 435/419, 418; 536/23.71; 800/205, DIG. 43, DIG. 42

[56] References Cited

U.S. PATENT DOCUMENTS

| 5,254,799 | 10/1993 | DeGreve et al. ........................ 800/205 |
| 5,380,831 | 1/1995 | Adang et al. .......................... 536/23.71 |
| 5,500,365 | 3/1996 | Fishhoff et al. ...................... 435/240.4 |

FOREIGN PATENT DOCUMENTS

| 305275 | 3/1989 | European Pat. Off. . |
| 359472 | 3/1990 | European Pat. Off. . |
| 385962 | 9/1990 | European Pat. Off. . |

OTHER PUBLICATIONS

*Plant Physiology*, vol. 85, 1987, pp. 1103–1109, Barton, K.A. et al., "Bacillus thuringiensis delta–endotoxin expressed in transgenic Nicotiana tabacum provides resistance to Lepidopteran insects".

*Nature*, vol. 328, Jul. 2, 1987, pp. 33–37, Vaeck, M. et al., "Transgenic plants protected from insect attack".

*Science*, Sep. 27, 1987, vol. 237, pp. 1570, Lewin, R., "When Does Homology means Something Else?".

Barton KA, et al. "*Bacillus thuringiensis* gamma–endotoxin expressed in trangenic *Nicotiana tabacum* provides resistance to lepidopteran insects." Plant Physiol. 85: 1103–1109, 1987.

Perlak FJ, et al. "Modification of the coding sequence enhances plant expression of insect control protein genes."PNAS 88: 3324–3328, Apr. 1991.

Murray EE, et al. "Codon usage in plant genes". Nucl. Acids Res. 17: 477–498, 1989.

Hofte H, et al. "Structural and fuctional analysis of a cloned delta endotoxin of *Bacillus thuringiensis* berliner 1715." Eur. J. Biochem. 161: 273–280, 1986.

*Primary Examiner*—David T. Fox
*Assistant Examiner*—Amy J. Nelson
*Attorney, Agent, or Firm*—Burns, Doane, Swecker & Mathis, LLP

[57] ABSTRACT

A DNA fragment, encoding all or an insecticidally-effective part of a Bt crystal protein, is modified by changing A and T sequences to corresponding G and C sequences encoding the same amino acids, in a region having transcriptional activity less than 25% of the transcriptional activity of a region at the translation initiation site.

2 Claims, 24 Drawing Sheets

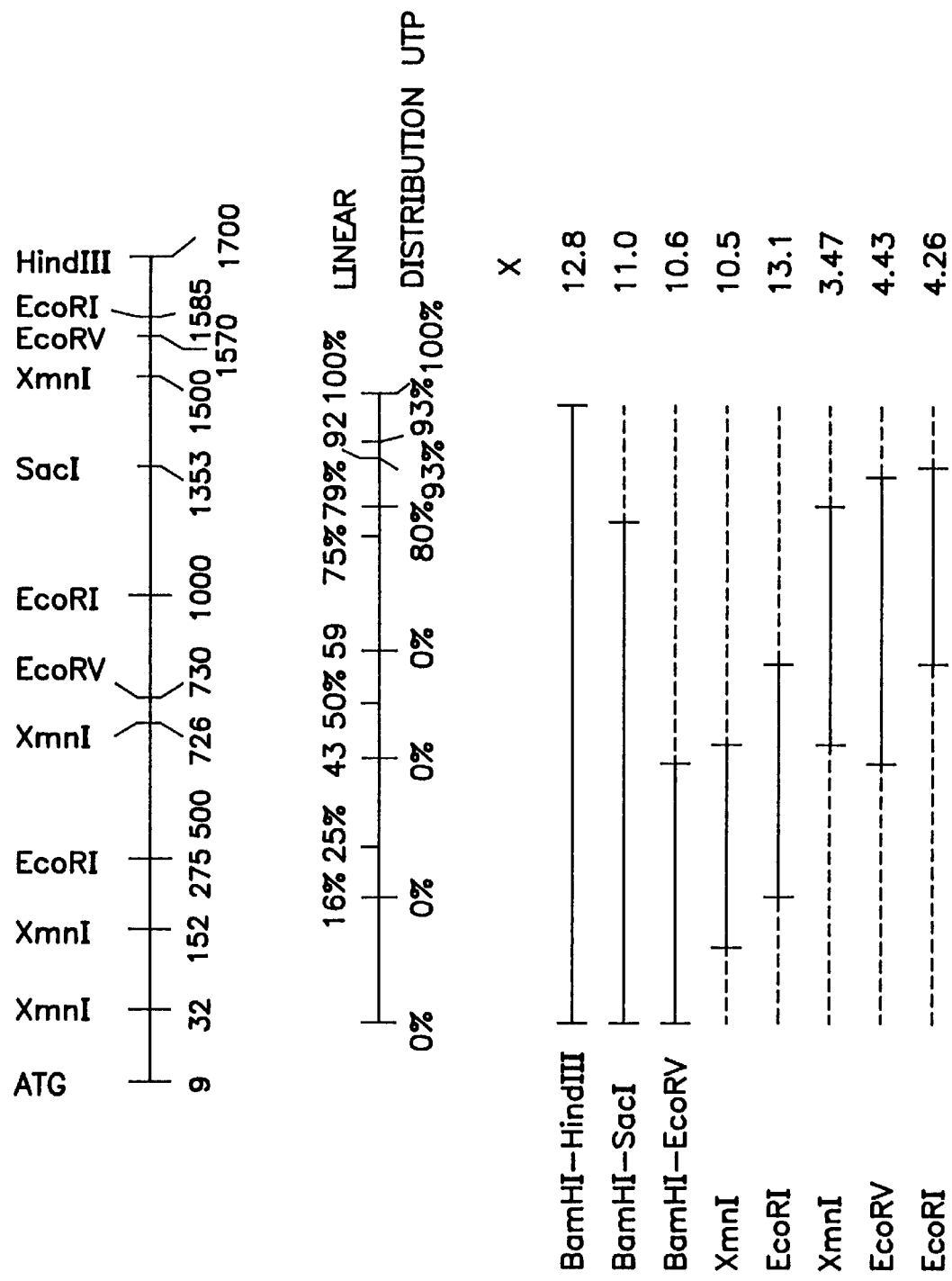
FIG. 2A-I

| RESTRICTION FRAGMENT | SIZE (bp) | #UTP | FRACTION #UTP SIZE (bp) | SCANNING VALUE AUTO-RADIOGRAM | X |
|---|---|---|---|---|---|
| BamHI–HindIII | 1700 | 513 | 0.302 | 6565 | 12.8 |
| BamHI–SacI | 1353 | 412 | 0.305 | 4572 | 11.0 |
| BamHI–EcoRV | 730 | 229 | 0.314 | 2466 | 10.6 |
| BamHI–EcoRI | 275 | 96 | 0.349 | – | – |
| XmnI–XmnI | 628 | 173 | 0.275 | 1817 | 10.5 |
| EcoRI–EcoRI | 725 | 224 | 0.309 | 2926 | 13.1 |
| XmnI–XmnI | 729 | 212 | 0.291 | 736 | 3.47 |
| EcoRV–EcoRV | 840 | 249 | 0.296 | 1102 | 4.43 |
| EcoRI–EcoRI | 585 | 149 | 0.255 | 635 | 4.26 |

FIG. 2A-2

SPLICED PVE36.SEQ 1:8600 INTO PVE36.SEQ
8600 BASE PAIRS

| | | | | | | | | | |
|---|---|---|---|---|---|---|---|---|---|
| 1 | : AatII | 8 | : BclI | 15 | : EcoRV | 22 | : NarI | 29 | : RsrII |
| 2 | : AccI | 9 | : BspMII | 16 | : Eco31I | 23 | : NdeI | 30 | : SacI |
| 3 | : AflII | 10 | : BssHII | 17 | : EspI | 24 | : NheI | 31 | : SpeI |
| 4 | : AlwNI | 11 | : BstEII | 18 | : HindII | 25 | : NsiI | 32 | : SphI |
| 5 | : ApaI | 12 | : BstXI | 19 | : HindIII | 26 | : PflMI | 33 | : Tth111I |
| 6 | : AvrII | 13 | : EagI | 20 | : KpnI | 27 | : PpuMI | 34 | : XcaI |
| 7 | : BamHI | 14 | : EcoNI | 21 | : NaeI | 28 | : PvuI | 35 | : XhoI |

| sample | gene assayed | ug loaded neo/cat | cpm (neo) | pg (cat) | cpm (cat) | pg (cat) | neo-SR1 | neo/cat | % rel to pJD51 |
|---|---|---|---|---|---|---|---|---|---|
| pJD50 | nptII/cat | 4/1 | 121 | 1.366 | 32 | 0.283 | 1.279 | 4.52 | 16.53 |
| pJD51 | nptII/cat | 4/1 | 131.3 | 1.482 | 20.7 | 0.051 | 1.395 | 27.35 | 100 |
| pJD52 | nptII/cat | 4/1 | 50.3 | 0.568 | 23.3 | 0.104 | 0.84 | 4.62 | 16.89 |
| pJD53 | nptII/cat | 4/1 | 44.3 | 0.5 | 36.7 | 0.379 | 0.431 | 1.09 | 3.99 |
| pJD54 | nptII/cat | 4/1 | 22 | 0.248 | 28.3 | 0.207 | 0.161 | 0.78 | 2.85 |
| pJD55 | nptII/cat | 4/1 | 374.3 | 4.225 | 35 | 0.344 | 4.138 | 12.03 | 43.99 |
| pJD56 | nptII/cat | 4/1 | 13.3 | 0.15 | 38 | 0.406 | 0.063 | 0.16 | 0.59 |
| pJD57 | nptII/cat | 4/1 | 55.7 | 0.629 | 21.7 | 0.071 | 0.542 | 7.63 | 27.9 |
| pJD58 | nptII/cat | 4/1 | 78.3 | 0.883 | 29.7 | 0.236 | 0.797 | 3.38 | 12.36 |
| pJD59 | nptII/cat | 4/1 | 17.3 | 0.195 | 38.3 | 0.412 | 0.108 | 0.26 | 0.95 |
| pJD60 | nptII/cat | 4/1 | 15.7 | 0.177 | 29 | 0.221 | 0.09 | 0.41 | 1.5 |
| pJD61 | nptII/cat | 4/1 | 286 | 3.228 | 42.3 | 0.494 | 3.141 | 6.36 | 23.25 |
| pJD62 | nptII/cat | 4/1 | 186.7 | 2.108 | 69 | 1.042 | 2.021 | 1.94 | 7.09 |
| pJD63 | nptII/cat | 4/1 | 117.7 | 1.329 | 43.3 | 0.515 | 1.242 | 2.41 | 8.81 |
| pJD64 | nptII/cat | 4/1 | 188.7 | 2.13 | 57.7 | 0.81 | 2.043 | 2.52 | 9.21 |
| pJD65 | nptII/cat | 4/1 | 158.7 | 1.791 | 42 | 0.488 | 1.704 | 3.49 | 12.76 |
| pJD66 | nptII/cat | 4/1 | 72.3 | 0.816 | 65 | 0.96 | 0.73 | 0.76 | 2.78 |
| pPS56D1 | nptII/cat | 4/1 | 24 | 0.271 | 56.7 | 0.79 | 0.184 | 0.23 | 0.84 |
| pPS56D2 | nptII/cat | 4/1 | 59.3 | 0.669 | 100 | 1.68 | 0.583 | 0.35 | 1.28 |
| pPS56D3 | nptII/cat | 4/1 | 214.3 | 2.419 | 49.3 | 0.64 | 2.332 | 3.66 | 13.38 |
| pPS56D4 | nptII/cat | 4/1 | 54.3 | 0.613 | 29.7 | 0.236 | 0.526 | 2.23 | 8.15 |
| pPS56D6 | nptII/cat | 4/1 | 37 | 0.418 | 46.7 | 0.584 | 0.331 | 0.57 | 2.08 |
| pPS56D7 | nptII/cat | 4/1 | 35.3 | 0.398 | 31.3 | 0.268 | 0.311 | 1.16 | 4.24 |
| pPS56D8 | nptII/cat | 4/1 | 43.3 | 0.489 | 45.7 | 0.564 | 0.402 | 0.71 | 2.6 |

FIG. 4

OLIGOPS15

GTACCAAAACCATGGCTATCGAGACCGGTTACACCCCAATCGATATCG

OLIGOPS16

ATCGATTGGGGTGTAACCGGTCTCGATAGCCATGGTTTTGGTACCGAT

```
                    Linear           LENGTH = 52
        1    5                                                          48    52
        ----= ==================================================----
           >------------------------------OLIGOPS15---------------------------->
           <---------------------------OLIGOPS16'------------------------<
     1     |--------------------------------------------------------------|  52
```

3) OLIGOPS16',  4) OLIGOPS15,

Name Base
3    1      ATCGGTACCA AAACCATGGC TATCGAGACC GGTTACACCC CAATCGAT
4    1           GTACCA AAACCATGGC TATCGAGACC GGTTACACCC CAATCGATAT CG

CON 1       ATCGGTACCA AAACCATGGC TATCGAGACC GGTTACACCC CAATCGATAT CG

ATC GGT ACC AAA ACC ATG GCT ATC GAG ACC GGT TAC ACC CCA ATC GAT ATC G
                    MET Ala Ile Glu Thr Gly Tyr Thr Pro Ile Asp Ile

FIG. 6A

OLIGO1

GATCCTCTAGAGACTGGATCAGGTACAACCAGTTCAGGAGGGAGTTAACCCTAACCGTGTTAGAC

OLIGO2

ATCGTGTCCCTATTCCCGAACTACGACAGCAGGACGTACCCAATCCGAACCGTGTCCCAGTTAACCAGGGA

OLIGO3

GATCTACACCAACCCAGTGTTAGAGAACTTCGACGGTAGCTTCCGAGGCTCGGCTCAGGGCATCG

OLIGO4

AGGGAAGCATCAGGAGCCCACACTTGATGGACATCCTTAACAGCATCACCATCTACACGGACGCT

OLIGO5

CACAGGGGAGAGTACTACTGGTCCGGGCACCAGATCATGGCTTCCCCTGTGGGGTTCTCGGGGCCAGAATTCG

OLIGO6

GATCCGAATTCTGGCCCCGAGAACCCCACAGGGGAAGCCATGATCTGGTGCCCGGACCAGTAGTAC

OLIGO7

TCTCCCCTGTGAGCGTCCGTGTAGATGGTGATGCTGTTAAGGATGTCCATCAAGTGTGGGCTCCT

OLIGO8

GATGCTTCCCTCGATGCCCTGAGCCGAGCCTCGGAAGCTACCGTCGAAGTTCTCTAACACTGGG

OLIGO9

TTGGTGTAGATCTCCCTGGTTAACTGGGACACGGTTCGGATTGGGTACGTCCTGCTGTCGTAGTTCGGGAA

OLIGO10

TAGGGACACGATGTCTAACACGGTTAGGGTTAACTCCCTCCTGAACTGGTTGTACCTGATCCAGTCTCTAGAG

FIG. 6B-1

```
synthe-9        Linear              LENGTH = 343

149        213           278
                          77     148        212           277
            5     66     137     202        267              343
          1       65 78  136     201        266              339
          #================================================#
           <--OLIGO10'---<<---OLIGO9'----<--OLIGO8'---<<--OLIGO7'----<--OLIGO6'---<
           >---OLIGO1--->----OLIGO2---->---OLIGO3--->---OLIGO4---->----OLIGO5---->

Name Base
1    1      GATCCTCTAG AGACTGGATC AGGTACAACC AGTTCAGGAG GGAGTTAACC CTAACCGTGT
10   1          CTCTAG AGACTGGATC AGGTACAACC AGTTCAGGAG GGAGTTAACC CTAACCGTGT

CON  1      GATCCTCTAG AGACTGGATC AGGTACAACC AGTTCAGGAG GGAGTTAACC CTAACCGTGT 1    61     TAGAC
10   57     TAGACATCGT GTCCCTA
2    1            ATCGT GTCCCTATTC CCGAACTACG ACAGCAGGAC GTACCCAATC CGAACCGTGT
9    1                        TTC CCGAACTACG ACAGCAGGAC GTACCCAATC CGAACCGTGT

CON  61     TAGACATCGT GTCCCTATTC CCGAACTACG ACAGCAGGAC GTACCCAATC CGAACCGTGT 2    56     CCCAGTTAAC CAGGGA
9    44     CCCAGTTAAC CAGGGAGATC TACACCAA
3    1                       GATC TACACCAACC CAGTGTTAGA GAACTTCGAC GGTAGCTTCC
8    1                             CC CAGTGTTAGA GAACTTCGAC GGTAGCTTCC

CON  121    CCCAGTTAAC CAGGGAGATC TACACCAACC CAGTGTTAGA GAACTTCGAC GGTAGCTTCC 3    45     GAGGCTCGGC TCAGGGCATC G
8    33     GAGGCTCGGC TCAGGGCATC GAGGGAAGCA TC
4    1                            AGGGAAGCA TCAGGAGCCC ACACTTGATG GACATCCTTA
7    1                                        AGGAGCCC ACACTTGATG GACATCCTTA

CON  181    GAGGCTCGGC TCAGGGCATC GAGGGAAGCA TCAGGAGCCC ACACTTGATG GACATCCTTA 4    40     ACAGCATCAC CATCTACACG GACGCT
7    29     ACAGCATCAC CATCTACACG GACGCTCACA GGGGAGA
5    1                                   CACA GGGGAGAGTA CTACTGGTCC GGGCACCAGA
6    1                                          GTA CTACTGGTCC GGGCACCAGA

CON  241    ACAGCATCAC CATCTACACG GACGCTCACA GGGGAGAGTA CTACTGGTCC GGGCACCAGA 5    35     TCATGGCTTC CCCTGTGGGG TTCTCGGGGC CAGAATTCG
6    24     TCATGGCTTC CCCTGTGGGG TTCTCGGGGC CAGAATTCGG ATC

CON  301    TCATGGCTTC CCCTGTGGGG TTCTCGGGGC CAGAATTCGG ATC
```

FIG. 6B-2

SYNTHE-9

```
                              27                                              54
GAT CCT CTA GAG ACT GGA TCA GGT ACA ACC AGT TCA GGA GGG AGT TAA CCC TAA
  Ser Ser Arg Asp Trp Ile Arg Tyr Asn Gln Phe Arg Arg Glu Leu Thr Leu Thr
                              81                                             108
CCG TGT TAG ACA TCG TGT CCC TAT TCC CGA ACT ACG ACA GCA GGA CGT ACC CAA
  Val Leu Asp Ile Val Ser Leu Phe Pro Asn Tyr Asp Ser Arg Thr Tyr Pro Ile
                             135                                             162
TCC GAA CCG TGT CCC AGT TAA CCA GGG AGA TCT ACA CCA ACC CAG TGT TAG AGA
  Arg Thr Val Ser Gln Leu Thr Arg Glu Ile Tyr Thr Asn Pro Val Leu Glu Asn
                             189                                             216
ACT TCG ACG GTA GCT TCC GAG GCT CGG CTC AGG GCA TCG AGG GAA GCA TCA GGA
  Phe Asp Gly Ser Phe Arg Gly Ser Ala Gln Gly Ile Glu Gly Ser Ile Arg Ser
                             243                                             270
GCC CAC ACT TGA TGG ACA TCC TTA ACA GCA TCA CCA TCT ACA CGG ACG CTC ACA
  Pro His Leu MET Asp Ile Leu Asn Ser Ile Thr Ile Tyr Thr Asp Ala His Arg
                             297                                             324
GGG GAG AGT ACT ACT GGT CCG GGC ACC AGA TCA TGG CTT CCC CTG TGG GGT TCT
  Gly Glu Tyr Tyr Trp Ser Gly His Gln Ile MET Ala Ser Pro Val Gly Phe Ser

CGG GGC CAG AAT TCG GAT C
  Gly Pro Glu Phe Gly
```

FIG. 6B-3

PVE36.SEQ   nucleotide 800 - 4000

```
AAATGGATAAATAGCCTTGCTTCCTATTATATCTTCCCAAATTACCAATACATTACACTAGCATCTGAAT
TTCATAACCAATCTCGATACACCAAATCGATGGATCCCGATAACAATCCGAACATCAATGAATGCATTCC
TTATAATTGTTTAAGTAACCCTGAAGTAGAAGTATTAGGTGGAGAAAGAATAGAAACTGGTTACACCCCA
ATCGATATTTCCTTGTCGCTAACGCAATTTCTTTTGAGTGAATTTGTTCCCGGTGCTGGATTTGTGTTAG
GACTAGTTGATATAATATGGGGAATTTTTGGTCCCTCTCAATGGGACGCATTTCTTGTACAAATTGAACA
GTTAATTAACCAAAGAATAGAAGAATTCGCTAGGAACCAAGCCATTTCTAGATTAGAAGGACTAAGCAAT
CTTTATCAAATTTACGCAGAATCTTTTAGAGAGTGGGAAGCAGATCCTACTAATCCAGCATTAAGAGAAG
AGATGCGTATTCAATTCAATGACATGAACAGTGCCCTTACAACCGCTATTCCTCTTTTTGCAGTTCAAAA
TTATCAAGTTCCTCTTTTATCAGTATATGTTCAAGCTGCAAATTTACATTTATCAGTTTTGAGAGATGTT
TCAGTGTTTGGACAAAGGTGGGGATTTGATGCCGCGACTATCAATAGTCGTTATAATGATTTAACTAGGC
TTATTGGCAACTATACAGATCATGCTGTACGCTGGTACAATACGGGATTAGAGCGTGTATGGGGACCGGA
TTCTAGAGATTGGATAAGATATAATCAATTTAGAAGAGAATTAACACTAACTGTATTAGATATCGTTTCT
CTATTTCCGAACTATGATAGTAGAACGTATCCAATTCGAACAGTTTCCCAATTAACAAGAGAAATTTATA
CAAACCCAGTATTAGAAAATTTTGATGGTAGTTTTCGAGGCTCGGCTCAGGGCATAGAAGGAAGTATTAG
GAGTCCACATTTGATGGATATACTTAACAGTATAACCATCTATACGGATGCTCATAGAGGAGAATATTAT
TGGTCAGGGCATCAAATAATGGCTTCTCCTGTAGGGTTTTCGGGGCCAGAATTCACTTTTCCGCTATATG
GAACTATGGGAAATGCAGCTCCACAACAACGTATTGTTGCTCAACTAGGTCAGGGCGTGTATAGAACATT
ATCGTCCACTTTATATAGAAGACCTTTTAATATAGGGATAAATAATCAACAACTATCTGTTCTTGACGGG
ACAGAATTTGCTTATGGAACCTCCTCAAATTTGCCATCCGCTGTATACAGAAAAAGCGGAACGGTAGATT
CGCTGGATGAAATACCGCCACAGAATAACAACGTGCCACCTAGGCAAGGATTTAGTCATCGATTAAGCCA
TGTTTCAATGTTTCGTTCAGGCTTTAGTAATAGTAGTGTAAGTATAATAAGAGCTCCTATGTTCTCTTGG
ATACATCGTAGTGCTGAATTTAATAATATAATTCCTTCATCACAAATTACACAAATACCTTTAACAAAAT
CTACTAATCTTGGCTCTGGAACTTCTGTCGTTAAAGGACCAGGATTTACAGGAGGAGATATTCTTCGAAG
AACTTCACCTGGCCAGATTTCAACCTTAAGAGTAAATATTACTGCACCATTATCACAAAGATATCGGGTA
AGAATTCGCTACGCTTCTACCACAAATTTACAATTCCATACATCAATTGACGGAAGACCTATTAATCAGG
GGAATTTTTCAGCAACTATGAGTAGTGGGAGTAATTTACAGTCCGGAAGCTTTAGGACTGTAGGTTTTAC
TACTCCGTTTAACTTTTCAAATGGATCAAGTGTATTTACGTTAAGTGCTCATGTCTTCAATTCAGGCAAT
GAAGTTTATATAGATCGAATTGAATTTGTTCCGGCAGAAGTAACCTTTGAGGCAGAATATGATTTAGAAA
GAGCACAAAAGGCGGTGAATGAGCTGTTTACTTCTTCCAATCAAATCGGGTTAAAAACAGATGTGACGGA
TTATCATATTGATCAAGTATCCAATTTAGTTGAGTGTTTATCTGATGAATTTTGTCTGGATGAAAAAAAA
GAATTGTCCGAGAAAGTCAAACATGCGAAGCGACTTAGTGATGAGCGGAAXXXXXCCTCGAGCTTGGATG
GATTGCACGCAGGTTCTCCGGCCGCTTGGGTGGAGAGGCTATTCGGCTATGACTGGGCACAACAGACAAT
CGGCTGCTCTGATGCCGCCGTGTTCCGGCTGTCAGCGCAGGGGCGCCCGGTTCTTTTTGTCAAGACCGAC
CTGTCCGGTGCCCTGAATGAACTGCAGGACGAGGCAGCGCGGCTATCGTGGCTGGCCACGACGGGCGTTC
CTTGCGCAGCTGTGCTCGACGTTGTCACTGAAGCGGGAAGGGACTGGCTGCTATTGGGCGAAGTGCCGGG
GCAGGATCTCCTGTCATCTCACCTTGCTCCTGCCGAGAAAGTATCCATCATGGCTGATGCAATGCGGCGG
CTGCATACGCTTGATCCGGCTACCTGCCCATTCGACCACCAAGCGAAACATCGCATCGAGCGAGCACGTA
CTCGGATGGAAGCCGGTCTTGTCGATCAGGATGATCTGGACGAAGAGCATCAGGGGCTCGCGCCAGCCGA
ACTGTTCGCCAGGCTCAAGGCGCGCATGCCCGACGGCGAGGATCTCGTCGTGACCCATGGCGATGCCTGC
TTGCCGAATATCATGGTGGAAAATGGCCGCTTTTCTGGATTCATCGACTGTGGCCGGCTGGGTGTGGCGG
ACCGCTATCAGGACATAGCGTTGGCTACCCGTGATATTGCTGAAGAGCTTGGCGGCGAATGGGCTGACCG
CTTCCTCGTGCTTTACGGTATCGCCGCTCCCGATTCGCAGCGCATCGCCTTCTATCGCCTTCTTGACGAG
TTCTTCTGACAGATCCCCCGATGAGCTAAGCTAGCTATATCATCAATTTATGTATTACACATAATATCGC
ACTCAGTCTTTCATCTACGGCAATGTACCAGCTGATATAATCAGTTATTGAAATATTTCTGAATTTAAAC
TTGCATCAATAAATTTATGTTTTTGCTTGGACTATAATACCTGACTTGTTATTTTATCAATAAATATTTA
AACTATATTTCTTTCAAGATGGGAATTAACATCTACAAATTGCCTTTTCTT
```

The ATG initiation codon and the TGA stop codon are underlined.

FIG. 6C-1

PPS029.SEQ nucleotide 800 - 4000

```
AAATGGATAAATAGCCTTGCTTCCTATTATATCTTCCCAAATTACCAATACATTACACTAGCATCTGAAT
TTCATAACCAATCTCGATACACCAAATCGGTACCAAAACCATGGCTATCGAGACCGGTTACACCCCAATC
GATATTTCCTTGTCGCTAACGCAATTTCTTTTGAGTGAATTTGTTCCCGGTGCTGGATTTGTGTTAGGAC
TAGTTGATATAATATGGGGAATTTTTGGTCCCTCTCAATGGGACGCATTTCTTGTACAAATTGAACAGTT
AATTAACCAAAGAATAGAAGAATTCGCTAGGAACCAAGCCATTTCTAGATTAGAAGGACTAAGCAATCTT
TATCAAATTTACGCAGAATCTTTTAGAGAGTGGGAAGCAGATCCTACTAATCCAGCATTAAGAGAAGAGA
TGCGTATTCAATTCAATGACATGAACAGTGCCCTTACAACCGCTATTCCTCTTTTTGCAGTTCAAAATTA
TCAAGTTCCTCTTTTATCAGTATATGTTCAAGCTGCAAATTTACATTTATCAGTTTTGAGAGATGTTTCA
GTGTTTGGACAAAGGTGGGGATTTGATGCCGCGACTATCAATAGTCGTTATAATGATTTAACTAGGCTTA
TTGGCAACTATACAGATCATGCTGTACGCTGGTACAATACGGGATTAGAGCGTGTATGGGGACCGGATTC
TAGAGACTGGATCAGGTACAACCAGTTCAGGAGGGAGTTAACCCTAACCGTGTTAGACATCGTGTCCCTA
TTCCCGAACTACGACAGCAGGACGTACCCAATCCGAACCGTGTCCCAGTTAACCAGGGAGATCTACACCA
ACCCAGTGTTAGAGAACTTCGACGGTAGCTTCCGAGGCTCGGCTCAGGGCATCGAGGGAAGCATCAGGAG
CCCACACTTGATGGACATCCTTAACAGCATCACCATCTACACGGACGCTCACAGGGGAGAGTACTACTGG
TCCGGGCACCAGATCATGGCTTCCCCTGTGGGGTTCTCGGGGCCAGAATTCACTTTTCCGCTATATGGAA
CTATGGGAAATGCAGCTCCACAACAACGTATTGTTGCTCAACTAGGTCAGGGCGTGTATAGAACATTATC
GTCCACTTTATATAGAAGACCTTTTAATATAGGGATAAATAATCAACAACTATCTGTTCTTGACGGGACA
GAATTTGCTTATGGAACCTCCTCAAATTTGCCATCCGCTGTATACAGAAAAAAGCGGAACGGTAGATTCGC
TGGATGAAATACCGCCACAGAATAACAACGTGCCACCTAGGCAAGGATTTAGTCATCGATTAAGCCATGT
TTCAATGTTTCGTTCAGGCTTTAGTAATAGTAGTGTAAGTATAATAAGAGCTCCTATGTTCTCTTGGATA
CATCGTAGTGCTGAATTTAATAATATAATTCCTTCATCACAAATTACACAAATACCTTTAACAAAATCTA
CTAATCTTGGCTCTGGAACTTCTGTCGTTAAAGGACCAGGATTTACAGGAGGAGATATTCTTCGAAGAAC
TTCACCTGGCCAGATTTCAACCTTAAGAGTAAATATTACTGCACCATTATCACAAAGATATCGGGTAAGA
ATTCGCTACGCTTCTACCACAAATTTACAATTCCATACATCAATTGACGGAAGACCTATTAATCAGGGGA
ATTTTTCAGCAACTATGAGTAGTGGGAGTAATTTACAGTCCGGAAGCTTTAGGACTGTAGGTTTTACTAC
TCCGTTTAACTTTTCAAATGGATCAAGTGTATTTACGTTAAGTGCTCATGTCTTCAATTCAGGCAATGAA
GTTTATATAGATCGAATTGAATTTGTTCCGGCAGAAGTAACCTTTGAGGCAGAATATGATTTAGAAAGAG
CACAAAAGGCGGTGAATGAGCTGTTTACTTCTTCCAATCAAATCGGGTTAAAAACAGATGTGACGGATTA
TCATATTGATCAAGTATCCAATTTAGTTGAGTGTTTATCTGATGAATTTTGTCTGGATGAAAAAAAAGAA
TTGTCCGAGAAAGTCAAACATGCGAAGCGACTTAGTGATGAGCGGAAXXXXXCCTCGAGCTTGGATGGAT
TGCACGCAGGTTCTCCGGCCGCTTGGGTGGAGAGGCTATTCGGCTATGACTGGCACAACAGACAATCGG
CTGCTCTGATGCCGCCGTGTTCCGGCTGTCAGCGCAGGGGCGCCCGGTTCTTTTTGTCAAGACCGACCTG
TCCGGTGCCCTGAATGAACTGCAGGACGAGGCAGCGCGGCTATCGTGGCTGGCCACGACGGGCGTTCCTT
GCGCAGCTGTGCTCGACGTTGTCACTGAAGCGGGAAGGGACTGGCTGCTATTGGGCGAAGTGCCGGGGCA
GGATCTCCTGTCATCTCACCTTGCTCCTGCCGAGAAAGTATCCATCATGGCTGATGCAATGCGGCGGCTG
CATACGCTTGATCCGGCTACCTGCCCATTCGACCACCAAGCGAAACATCGCATCGAGCGAGCACGTACTC
GGATGGAAGCCGGTCTTGTCGATCAGGATGATCTGGACGAAGAGCATCAGGGGCTCGCGCCAGCCGAACT
GTTCGCCAGGCTCAAGGCGCGCATGCCCGACGGCGAGGATCTCGTCGTGACCCATGGCGATGCCTGCTTG
CCGAATATCATGGTGGAAAATGGCCGCTTTTCTGGATTCATCGACTGTGGCCGGCTGGGTGTGGCGGACC
GCTATCAGGACATAGCGTTGGCTACCCGTGATATTGCTGAAGAGCTTGGCGGCGAATGGGCTGACCGCTT
CCTCGTGCTTTACGGTATCGCCGCTCCCGATTCGCAGCGCATCGCCTTCTATCGCCTTCTTGACGAGTTC
TTCTGACAGATCCCCCGATGAGCTAAGCTAGCTATATCATCAATTTATGTATTACACATAATATCGCACT
CAGTCTTTCATCTACGGCAATGTACCAGCTGATATAATCAGTTATTGAAATATTTCTGAATTTAAACTTG
CATCAATAAATTTATGTTTTTGCTTGGACTATAATACCTGACTTGTTATTTTATCAATAAATATTTAAAC
TATATTTCTTTCAAGATGGGAATTAACATCTACAAATTGCCTTTTCTTATCGACCATGTACGGGTACCGA
GCTCGAATTCCTACGCAGCAGGTCTCATCAAGACGATCTACCCGAGTAACA
``` the ATG initiation codon and the TGA stop codon are underlined.

FIG.6C-2

Plot of AT/ATGC in sequence pVE36, from base 800 to base 4000 computed using an interval of 50 bases.

REGION A : N-terminal deletion + modification
REGION B : internal modification

Plot of AT/ATGC in sequence PPS029.
From base 800 to base 4000 computed using an interval of 50 bases.

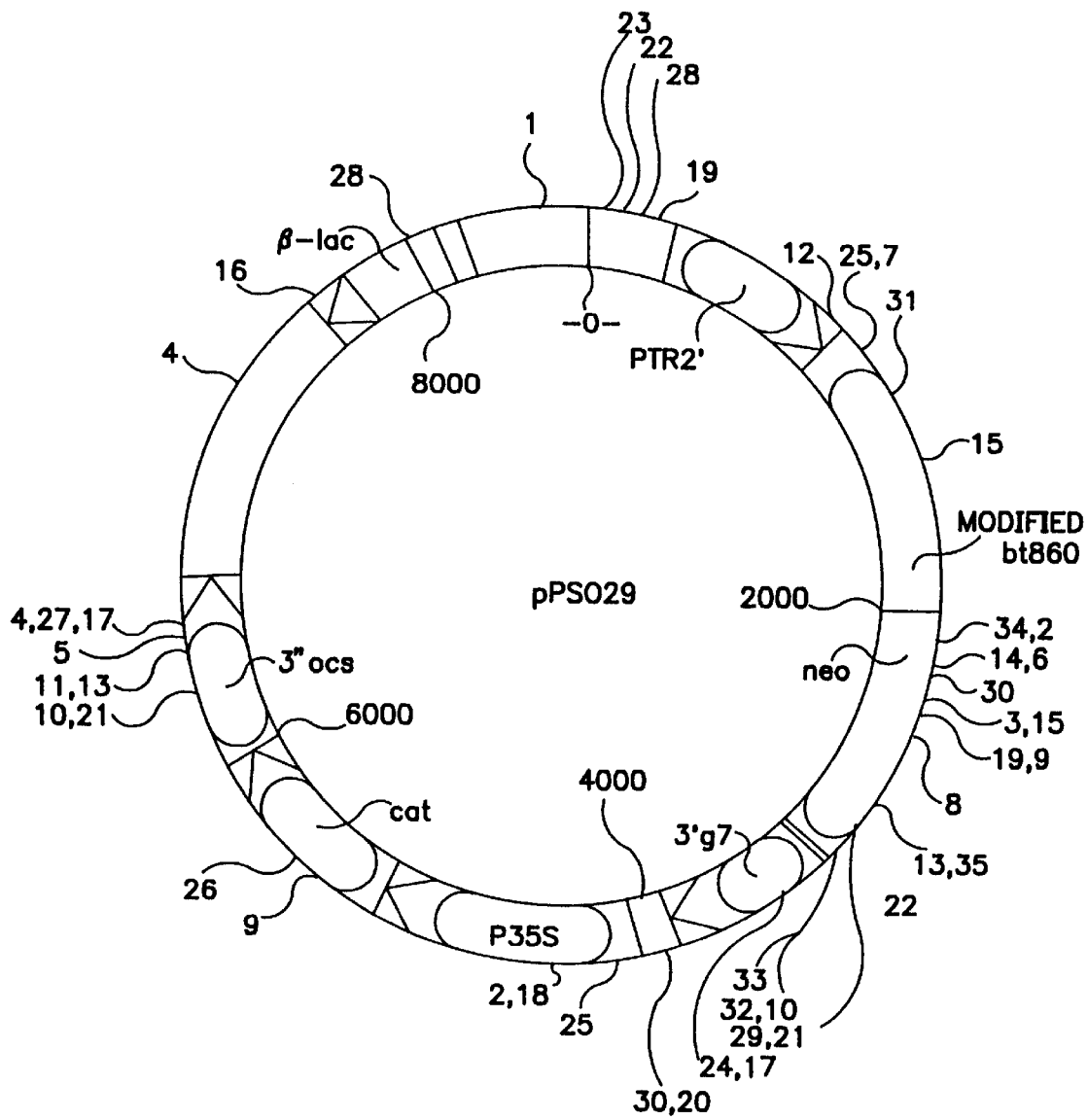
| | | | | | |
|---|---|---|---|---|---|
| 1 : AatII | 8 : BclI | 15 : EcoRV | 22 : NarI | 29 : RsrII |
| 2 : AccI | 9 : BspMII | 16 : Eco31I | 23 : NdeI | 30 : SacI |
| 3 : AflII | 10 : BssHII | 17 : EspI | 24 : NheI | 31 : SpeI |
| 4 : AlwNI | 11 : BstEII | 18 : HindII | 25 : NsiI | 32 : SphI |
| 5 : ApaI | 12 : BstXI | 19 : HindIII | 26 : PflMI | 33 : Tth111I |
| 6 : AvrII | 13 : EagI | 20 : KpnI | 27 : PpuMI | 34 : XcaI |
| 7 : BamHI | 14 : EcoNI | 21 : NaeI | 28 : PvuI | 35 : XhoI |
FIG. 8A-I

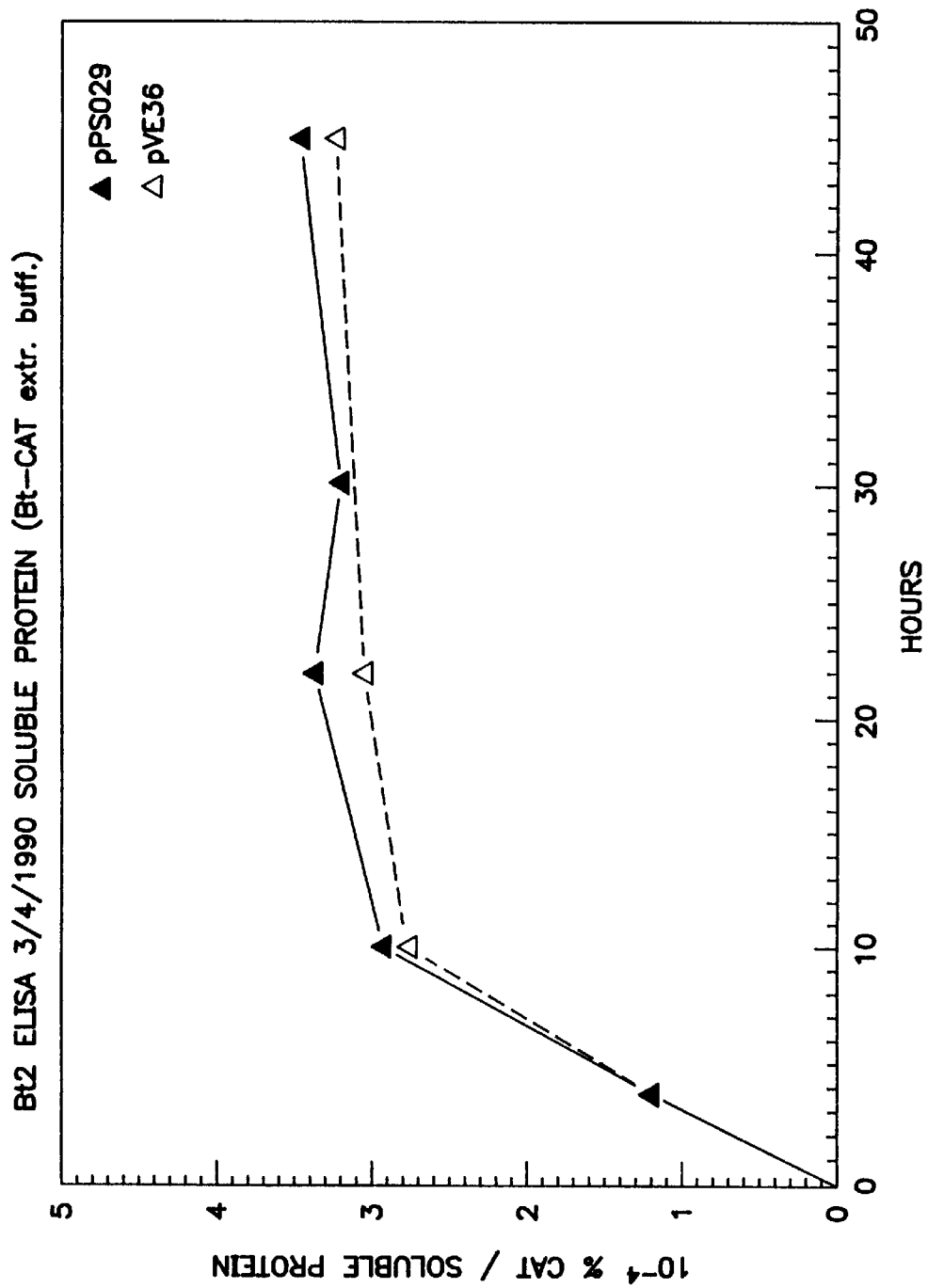
FIG. 8B-I

MODIFIED BACILLUS THURINGIENSIS INSECTICIDAL-CRYSTAL PROTEIN GENES AND THEIR EXPRESSION IN PLANT CELLS

This application is a divisional of application Ser. No. 08/453,104, filed May 30, 1995 issued as U.S. Pat. No. 5,663,446; which is a continuation of application Ser. No. 07/937,869, filed as PCT/EP91/00733 Apr. 17, 1991, now abandoned.

This invention provides a modified *Bacillus thuringiensis* ("Bt") gene (the "modified BtICP gene") encoding all or an insecticidally-effective portion of a Bt insecticidal crystal protein ("ICP"). A plant, transformed with the modified Bt ICP gene can show higher expression levels of the encoded ICP and improved insect-resistance.

BACKGROUND OF THE INVENTION

Plant genetic engineering technology has made significant progress during the last 10 years. It has become possible to introduce stably foreign genes into plants. This has provided exciting opportunities for modern agriculture. Derivatives of the Ti-plasmid of the plant pathogen, *Agrobacterium tumefaciens*, have proven to be efficient and highly versatile vehicles for the introduction of foreign genes into plants and plant cells. In addition, a variety of free DNA delivery methods, such as electroporation, microinjection, pollen-mediated gene transfer and particle gun technology, have been developed for the same purpose.

The major aim of plant transformations by genetic engineering has been crop improvement. In an initial phase, research has been focused on the engineering into plants of useful traits such as insect-resistance. In this respect, progress in engineering insect resistance in transgenic plants has been obtained through the use of genes, encoding ICPs, from Bt strains (Vaeck et al., 1987). A Bt strain is a spore forming gram-positive bacterium that produces a parasporal crystal which is composed of crystal proteins which are specifically toxic against insect larvae. Bt ICPs possess a specific insecticidal spectrum and display no toxicity towards other animals and humans (Gasser and Fraley, 1989). Therefore, the Bt ICP genes are highly suited for plant engineering purposes.

For more than 20 years, Bt crystal spore preparations have been used as biological insecticides. The commercial use of Bt sprays has however been limited by high production costs and the instability of crystal proteins when exposed in the field (Vaeck et al., 1987). The heterogeneity of Bt strains has been well documented. Strains active against Lepidoptera (Dulmage et al., 1981), Diptera (Goldberg and Margalit, 1977) and Coleoptera (Krieg et al., 1983) have been described.

Bt strains produce endogenous crystals upon sporulation. Upon ingestion by insect larvae, the crystals are solubilized in the alkaline environment of the insect midgut giving rise to a protoxin which is subsequently proteolytically converted into a toxic core fragment or toxin of 60–70 kDa. The toxin causes cytolysis of the epithelial midgut cells. The specificity of Bt ICPs can be determined by their interaction with high-affinity binding sites present on insects' midgut epithelia.

The identification of Bt ICPs and the cloning and sequencing of Bt ICP genes has been reviewed by Höfte and Whiteley (1989). The Bt ICP genes share a number of common properties. They generally encode insecticidal proteins of 130 kDa to 140 kDa or of about 70 kDa, which contain toxic fragments of 60±10 kDa (Höfte and Whiteley, 1989). The Bt ICP genes have been classified into four major groups according to both their structural similarities and insecticidal spectra (Höfte and Whiteley, 1989): Lepidoptera-specific (CryI), Lepidoptera- and Diptera-specific (CryII), Coleoptera-specific (CryIII) and Diptera-specific (Cry IV) genes. The Lepidoptera-specific genes (CryI) all encode 130–140 kDa proteins. These proteins are generally synthesized as protoxins. The toxic domain is localized in the N-terminal half of the protoxin. Deletion analysis of several CryI genes confirm that 3' portions of the protoxins are not absolutely required for toxic activity (Schnepf et al., 1989). Cry II genes encode 65 kDa proteins (Widner and Whiteley, 1985). The Cry II A proteins are toxic against both Lepidoptera and Diptera while the Cry II B proteins are toxic only to Lepidopteran insects. The Coleoptera-specific genes (Cry III) generally encode proteins vith a molecular weight of about 70 kDa. (Whiteley and Höfte, 1989). The corresponding gene (cry III A) expressed in *E. coli* directs the synthesis of a 72 kDa protein which is toxic for the Colorado potato beetle. This 72 kDa protein is processed to a 66 kDa protein by spore-associated bacterial proteases which remove the first 57 N-terminal amino acids (Mc Pherson et al., 1988). Deletion analysis demonstrated that this type of gene cannot be truncated at its 3'-end without the loss of toxic activity (Höfte and Whiteley, 1989). Recently, an anti-coleopteran strain, which produces a 130 kDa, protein has also been described (European patent application ("EPA") 89400428.2). The cry IV class of crystal protein genes is composed of a heterogenous group of Diptera-specific crystal protein genes (Höfte and Whiteley, 1989).

The feasibility of generating insect-resistant transgenic crops by using Bt ICPs has been demonstrated. (Vaeck et al., 1987; Fischoff et al., 1987 and Barton et al., 1987). Transgenic plants offer an attractive alternative and provide an entirely new approach to insect control in agriculture which is at the same time safe, environmentally attractive and cost-effective. (Meeusen and Warren, 1989). Successful insect control has been observed under field conditions (Delannay et al., 1989; Meeusen and Warren, 1989).

In all cases, Agrobacterium-mediated gene transfer has been used to express chimaeric Bt ICP genes in plants (Vaeck et al., 1987; Barton et al., 1987; Fischoff et al., 1987). Bt ICP genes were placed under the control of a strong promoter capable of directing gene expression in plant cells. It is however remarkable that expression levels in plant cells were high enough only to obtain insect-killing levels of Bt ICP genes when truncated genes were used (Vaeck et al., 1987; Barton et al., 1987). None of the transgenic plants containing a full-length Bt ICP gene produced insect-killing activity. Moreover, Barton et al. (1987) showed that tobacco calli transformed with the entire Bt ICP coding sequence became necrotic and died. These results indicate that the Bt ICP gene presents unusual problems that must be overcome to obtain significant levels of expression in plants. Even, when using a truncated Bt ICP gene for plant transformation, the steady state levels of Bt ICP mRNA obtained in transgenic plants are very low relative to levels produced by both an adjacent NPT II-gene, used as a marker, and by other chimeric genes (Barton et al., 1987; Vaeck et al., 1987). Moreover, the Bt ICP mRNA cannot be detected by northern blot analysis. Similar observations were made by Fischoff et al. (1987); they reported that the level of Bt ICP mRNA was much lower than expected for a chimeric gene expressed from the CaMV35S promoter. In other words, the cytoplasmic accumulation of the bt mRNA, and consequently the synthesis, the accumulation and thereby the expression of the Bt ICP protein in plant cells, are extremely inefficient. By contrast, in microorganisms, it has been shown that truncated Bt ICP genes are less favorable than full-length genes (Adang et al., 1985), indicating that the inefficient expression is solely related to the heterologous expression of Bt ICP genes in plants.

The problem of obtaining significant Bt ICP expression levels in plant cells seems to be inherent and intrinsic to the Bt ICP genes. Furthermore, the relatively low and poor expression levels obtained in plants appears to be a common phenomenon for all Bt ICP genes.

It is known that there are six steps at which gene expression can be controlled in eucaryotes (Darnell, 1982):

1) Transcriptional control
2) RNA processing control
3) RNA transport control
4) mRNA degradation control
5) translational control
6) protein activity control For all genes, transcriptional control is considered to be of paramount importance (The Molecular Biology of the Cell, 1989).

In European patent publications ("EP") 385,962 and 359,472, efforts to modify the codon usage of Bt ICP genes to improve their expression in plant cells have been reported. However, wholesale (i.e., non-selective) changes in codon usage can introduce cryptic regulatory signals in a gene, thereby causing problems in one or more of the six steps mentioned above for gene expression, and thus inhibiting or interfering with transcription and/or translation of the modified foreign gene in plant cells. For example, changes in codon usage can cause differential rates of mRNA production, producing instability in the mRNA, so produced (e.g., by exposure of regions of the mRNA, unprotected by ribosomes, to attack and degradation by cytoplasmic enzymes). Changes in codon usage also can inadvertently cause inhibition or termination of RNA polymerase II elongation on the so-modified gene.

SUMMARY OF THE INVENTION

In accordance with this invention is provided a process for modifying a foreign gene, particularly a Bt ICP gene, whose level and/or rate of expression in plant cells, transformed with the gene, is limited by the rate and/or level of nuclear production of an mRNA encoded by the gene; the process comprises the step of changing adenine and thymine sequences to corresponding guanine and cytosine sequences encoding the same amino acids in a plurality of translational codons of the gene that would otherwise directly or indirectly cause a nuclear event which would negatively control (i.e., inhibit or interfere with) transcription, nuclear accumulation and/or nuclear export of the mRNA, particularly transcription, quite particularly elongation of transcription by RNA polymerase II of the plant cells. Preferably, the adenine and thymine sequences are changed to cytosine and guanine sequences in translational codons of at least one region of the gene which, during transcription, would otherwise have thereon a relatively low percentage of RNA polymerase II as compared to another adjacent upstream (i.e., 5') region of the gene.

Also in accordance with this invention is provided the modified Bt ICP gene resulting from the process.

Further in accordance with this invention, a process is provided for improving the resistance of a plant against insect pests by transforming the plant cell genome with at least one modified Bt ICP gene.

This invention also relates to a chimaeric gene that can be used to transform plant cells and that contains the following operably-linked DNA fragments in the same transcriptional unit:

1) the modified Bt ICP gene;
2) a promoter suitable for directing transcription of the modified Bt ICP gene in the plant cells; and
3) suitable transcript 3' end formation and polyadenylation signals for expressing the modified Bt ICP gene in the plant cells.

This invention further relates to:

a cell of a plant, the nuclear genome of which has been transformed to contain, preferably stably integrated therein, the modified St ICP gene, particularly the chimaeric gene;

cell cultures consisting of the plant cell;

a plant which is regenerated from the transformed plant cell or is produced from the so-regenerated plant, the genome of which contains the modified Bt ICP gene, particularly the chimaeric gene, and which shows improved resistance to insect pests;

seeds of the plant; and a vector for stably transforming the nuclear genome of plant cells with the modified Bt ICP gene, particularly the chimaeric gene.

DETAILED DESCRIPTION OF THE INVENTION

Figure 1:
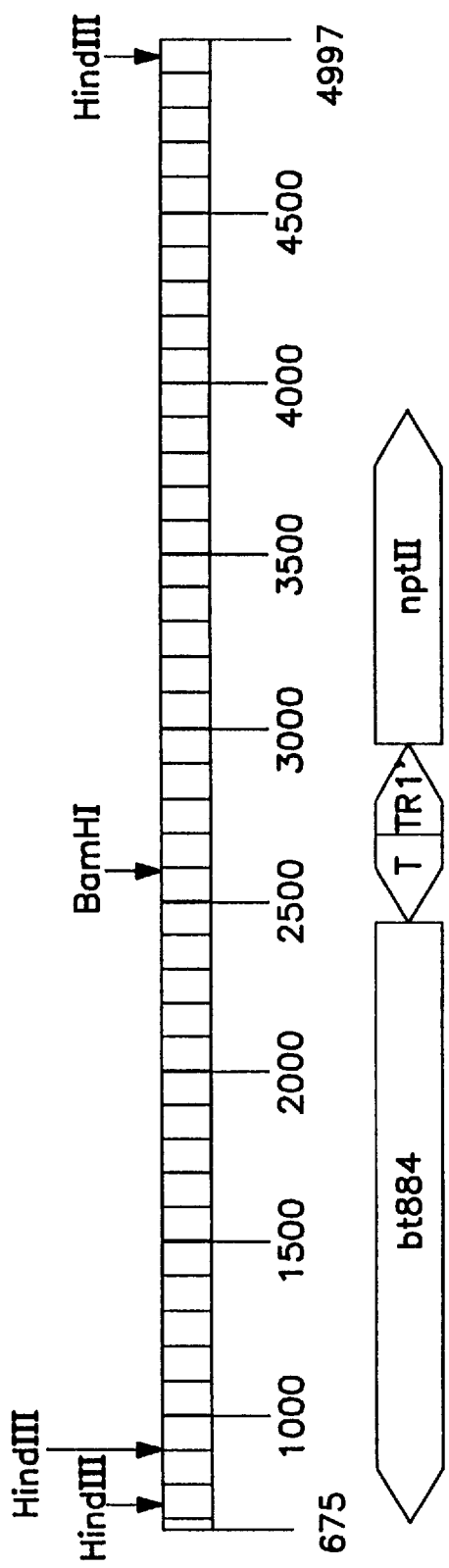

As used herein, "Bt ICP" should be understood as an intact protein or a part thereof which has insecticidal activity and which can be produced in nature by *B. thuringiensis*. A Bt ICP can be a protoxin, as well as an active toxin or other insecticidal truncated part of a protoxin which need not be crystalline and which need not be a naturally occurring protein. An example of a Bt ICP is a Bt2 insecticidal crystal protein (Höfte et al., 1986), as well as its insecticidally effective parts which are truncated at its C- and/or N-terminal ends towards its tryspsin cleavage site(s) and preferably having a molecular weight of 60–80 kDa. Other examples of Bt ICPs are: Bt2, Bt3, Bt4, Bt13, Bt14, Bt15, Bt18, Bt21, Bt22, Bt73, Bt208, Bt245, BtI260 and BtI109P as disclosed in PCT publications WO90/15139 and WO90/09445, in Höfte and Whiteley (1989) and in EPA 90403724.9.

As used herein, "protoxin" should be understood as the primary translation product of a full-length gene encoding a Bt ICP.

As used herein, "toxin" or "active toxin" or "toxic core" should all be understood as a part of a protoxin which can be obtained by protease (e.g., by trypsin) cleavage and has insecticidal activity.

As used herein, "truncated Bt gene" should be understood as a fragment of a full-length Bt gene which still encodes at least the toxic part of the Bt ICP, preferentially the toxin.

As used herein, "modified Bt ICP gene" should be understood as a DNA sequence which encodes a Bt ICP, and in which the content of adenine ("A") and thymine ("T") has been changed to guanine ("G") and cytosine ("C") in codons, preferably at least 3, in at least one region of the DNA sequence without affecting the original amino acid sequence of the Bt ICP. Preferably in at least two regions, especially in at least three regions, of the DNA sequence, the A and T content is changed to G and C in at least 3 codons. For regions downstream of the translation initiation site of the DNA sequence, it is preferred that the A-T content of at least about 10 codons, particularly at least about 33 codons, be changed to G-C.

By "region" of a modified Bt ICP gene is meant any sequence encoding at least three translational codons which affect expression of the gene in plants.

In accordance with this invention, it has been shown by means of mRNA turn-over studies that the expression pathway of a Bt ICP gene, such as bt2, bt14, bt15 and bt18, is specifically inhibited at the nuclear level in plant cells. In a further analysis, nuclei of transgenic tobacco plants, i.e., N28–220 (Vaeck et al., 1987), were used in a nuclear run-on assay to determine the distribution and the relative efficiency of RNA polymerase II complexes to initiate transcription of chimaeric Bt ICP plant genes. In this regard, the run-on assay has been used to determine initially the relative efficiency of RNA polymerase II complexes to initiate transcription of Bt ICP genes and thereafter to determine the relative distribution and migration efficiency of the RNA polymerase II complexes on the Bt ICP genes.

N28–220 contains the bt884 fragment under control of the TR 2' promoter as a chimaeric gene. Bt884 is a 5' fragment of the bt2 gene (Höfte et al., 1986) up to codon 610 (Vaeck et al., 1987). Using nuclear run-on analysis, isolated nuclei of N28–220 were incubated with highly labeled radioactive RNA precursors, so that the RNA transcripts being synthesized at the time became radioactively labeled. The RNA polymerase II molecules caught in the act of transcription in the cell continue elongating the same RNA molecules in vitro.

The nuclear run-on assays of nuclei of N28–220 culture (non-induced cells and induced cells, TR1'-neo, TR2'-bt884) revealed that transcription from the TR1' and TR2' promoters is about equally efficient. This implies that the low Bt ICP (i.e., Bt884) expression levels are not due to a specifically reduced transcriptional activity of the TR2' promoter. However, nuclear run-on analysis with N28–220 nuclei indicated that transcription elongation of the nascent Bt ICP mRNA is impaired somewhere between 700 to 1000 nucleotides downstream of the start of transcription. This means that RNA polymerase II is not able to transcribe the Bt ICP coding sequence with 100% efficiency. Filter binding assays using labeled Bt DNA fragments spanning this region and protein extract prepared from tobacco nuclei reveal that this DNA region undergoes specific interactions with proteins present in nuclei. These interactions are the prime candidates that cause or affect the impaired elongation of transcription by RNA polymerase II through this region. By modification of this region to abolish specific protein binding, Bt ICP expression levels will increase. However, other mechanisms responsible for impaired elongation in this region cannot be excluded.

Further in accordance with this invention, sequences within the coding region involved in negative control of cytoplasmic Bt ICP mRNA levels have been identified by deletion analysis. To this end, 24 deletion derivatives of pVE36 have been constructed. Three main types of deletion mutants have been constructed (see FIG. 3):

5' end deletions

3' end deletions internal deletions.

The expression of a mutant hybrid bt2-neo gene (encoding a fusion protein of Bt2 (Höfte et al., 1986) and NPTII) has been studied by means of transient expression experiments using the cat gene as a reference. To this end, the neo mRNA levels were measured in relation to cat mRNA levels in RNA extracts of SR1 protoplasts. The ratio between the neo and cat mRNA level was used to quantify on a relative basis the nptII transcript (i.e., mRNA) levels produced by the different constructions. These experiments show that progressive deletions of the carboxy-terminal (i.e., 3') part or the amino-terminal (i.e., 5') part of the Bt ICP coding sequence result in a gradual increase of the nptII transcript level. Furthermore, since the changes in transcript levels are not very abrupt, these results suggest that the low transcript levels produced by Bt ICP genes are not controlled by a single factor. Nevertheless, individual modifications of bt2 coding sequence can significantly reduce the interference and/or inhibition of the expression of the mRNA encoded by Bt ICP genes in plant cells at the level of transcript elongation, nuclear accumulation and nuclear export. The modification(s) may also affect cytoplasmic regulation and metabolism of such mRNAs and their translation.

Deletion analysis clearly indicates that several internal sequences, located within the Bt ICP coding region, might be involved in the negative regulation of the Bt ICP expression. By way of example, a 326 bp region (FIG. 6*b*) was identified in the bt2 gene that is involved in the negative control of BT ICP expression and that is located between nucleotide position 674 and nucleotide position 1000, particularly a 268 bp region between nucleotide positions 733 and 1000, quite particularly a 29 bp region between nucleotide positions 765 and 794 which carries two perfect CCAAT boxes which are known to be able to cause a reduction in elongation efficiency and termination of transcription by RNA polymerase II in animal systems (Connelly and Manley, 1989). This internal gene fragment or inhibitory zone may itself comprise a plurality of inhibitory zones which reduce Bt ICP expression levels or which interact directly or indirectly with other zones to inhibit or interfere with expression. Codon usage of this inhibitory zone has been modified in a second step by substituting A-T with G-C without affecting the amino acid sequence. In this regard, this internal 326 bp fragment (FIG. 6*b*) has been replaced with a modified Bt ICP fragment of this invention containing 63 modified codons. The effect of such modification of this inhibitory zone on Bt ICP expression has been analyzed both in transient and stable plant transformants. The results show that such modification of codon usage causes a significant increase of Bt ICP expression levels and hence improved insect-resistance.

In addition, N-terminal deletion mutants of the bt2 gene have been made by deleting the first N-terminal 28 amino acids (Höfte et al., 1986). It is known for the bt2 gene that the first 28 codons can be deleted without loss of toxicity (Höfte et al., 1986; Vaeck et al., 1987). Also, codon usage for three codons, 29 to 31, has been changed in accordance with this invention by replacing A-T with G-C without affecting the amino acid sequence. Furthermore, an optimal translation initiation (ATG) site was created based on the consensus sequence of Joshi (1987) as shown in FIG. 6*a*. Plants transformed with this modified Bt ICP gene show significantly higher Bt ICP expression levels.

In accordance with this invention, all or part of modified Bt ICP gene of the invention can be stably inserted in a conventional manner into the nuclear genome of a plant cell, and the so-transformed plant cell can be used to produce a transgenic plant showing improved expression of the Bt ICP gene. In this regard, a disarmed Ti-plasmid, containing the modified Bt ICP gene, in Agrobacterium (e.g., *A. tumefaciens*) can be used to transform a plant cell using the procedures described, for example, in EP 116,718 and EP 270,822, PCT publication 84/02913, EPA 87400544.0 and Gould et al. (1991) (which are incorporated herein by reference). Preferred Ti-plasmid vectors contain the foreign DNA sequence between the border sequence, or at least located to the left of the right border sequence, of the T-DNA of the Ti-plasmid. Of course, other types of vectors can be used to transform the plant cell, using procedures such as direct gene transfer (as described, for example, in EP 233, 247), pollen mediated transformation (as described, for example, in EP 270,356, PCT publication WO 85/01856, and U.S. Pat. No. 4,684,611), plant RNA virus-mediated transformation (as described, for example, in EP 67,553 and U.S. Pat. No. 4,407,956), liposome-mediated transformation (as described, for example, in U.S. Pat. No. 4,536,475) and other methods such as the recently described methods for transforming certain lines of corn (Fromm et al., 1990; Gordon-Kamm et al., 1990).

Preferably, the modified Bt ICP gene is inserted in a plant genome downstream of, and under the control of, a promoter which can direct the expression of the gene in the plant cells. Preferred promoters include, but are not limited to, the strong constitutive 35S promoter (Odell et al., 1985) of cauliflower mosaic virusl; 35S promoters have been obtained from different isolates (Hull and Howell, Virology 86, 482–493 (1987)). Other preferred promoters include the TR1' promoter and the TR2' promoter (Velten et al., 1984). Alternatively, a promoter can be utilized which is not constitutive but rather is specific for one or more tissues or organs. For example, the modified Bt ICP gene can be selectively expressed in the green tissues of a plant by placing the gene under the control of a light-inducible promoter such as the promoter of the ribulose-1,5-phosphate-carboxylase small subunit gene as described in EPA 86300291.1. Another alternative is to use a promoter whose expression is inducible by temperature or chemical factors.

It is also preferred that the modified Bt ICP gene be inserted upstream of suitable 3' transcription regulation signals (i.e., transcript 3' end formation and polyadenylation signals) such as the 3' untranslated end of the octopine synthase gene (Gielen et al., 1984) or T-DNA gene 7 (Velten and Schell, 1985).

The resulting transformed plant of this invention shows improved expression of the modified Bt ICP gene and hence is characterized by the production of high levels of Bt ICP. Such a plant can be used in a conventional breeding scheme to produce more transformed plants with the same improved insect-resistance characteristics or to introduce the modified Bt ICP gene into other varieties of the same or related plant species. Seeds, which are obtained from the transformed plants, contain the modified BtICP gene as a stable genomic insert.

Furthermore, at least two modified BtICP genes, coding for two non-competitively binding anti-Lepidopteran or anti-Coleopteran Bt ICPS, can be cloned into a plant expression vector (EPA 89401499.2). Plants transformed with such a vector are characterized by the simultaneous expression of at least two modified BtICP genes. The resulting transgenic plant is particularly useful to prevent or delay development of resistance to Bt ICP of insects feeding on the plant.

BRIEF DESCRIPTION OF THE DRAWINGS

FIG. 1—Comparison of the transcription initiation frequency of RNA polymerase II complexes in nuclei of N28–220. Hybridisation efficiencies of labeled nptII mRNA and Bt ICP mRNA with their complementary DNA counterparts present on a Southern blot were compared. DNA fragments were obtained from a digest of plasmid pGSH163. A schematic view of the region is given. The lengths of the fragments blotted on Hybond-H filter (1), the homologous genes on plasmid pGSH163 (2), and the densitometric values (3) are as follows:

| Digest: | 1 | 2 | 3 |
|---|---|---|---|
| BamHI/HindIII | 2358 | neo | 12386 |
| | 1695 | bt2 | 6565 |
| | 154 | bt2 | — |
| | 6250 | vector | — |

FIGS. 2A–2C.—FIG. 2*a*—Determination of the distribution of the RNA polymerase II complexes on the Bt ICP coding sequence in nuclei of N28–220. The hybridisation of labeled RNA prepared by nuclear run on with DNA fragments of the Bt ICP coding sequence was quantitated. The restriction fragments and scanning values are given in the table (FIG. 2A-2) and figure (FIG. 2A-1). The scanning value is proportional to "X", the size of the DNA fragment and the # UTP per RNA fragment hybridising. "X" is directly proportional to the number of RNA polymerases passing through the DNA fragment. "X" is proportional to the scanning value divided by the number of UTPS. The X values of the different restriction fragments are shown in the figure. In this regard, conversion of the different densitometric values into relative hybridisation efficiencies by normalising the values of the number of dATPs present in the DNA fragment, complementary to the hybridising RNA, generates the value "X". "X" is a relative measure of the number and the length of the extension of the transcripts. "X" thus reflects the number of RNA polymerases transcribing a specific DNA sequence and their elongation rate. DNA fragments present on the Southern digests of plasmid DNA of plant vector pGSH163 each have the following lengths of fragments blotted on Hybond-N filter (1), homologous genes on plasmid pGSH163 (2) and densitometric values (3):

| Digest: | 1 | 2 | 3 |
|---|---|---|---|
| BamHI/EcoRI | 8877 | neo | 15333 |
| | 726 | bt2(2) | 2926 |
| | 583 | bt2(3) | 635 |
| | 271 | bt2(1) | — |
| BamHI/EcoRV | 8887 | neo | 15182 |
| | 84 | bt2 | 2466 |
| | 729 | bt2 | 1102 |
| BamHI/HindIII | 6250 | — | — |
| | 2358 | neo | 12386 |
| | 1695 | bt2 | 6565 |
| | 154 | — | — |
| BamHI/SacI | 8053 | neo | 14194 |
| | 1353 | bt2(1) | 4572 |
| | 1051 | bt2(2) | 615 |
| XmnI | 4973 | neo | 13219 |
| | 2107 | — | — |
| | 1401 | — | — |
| | 729 | bt2(3) | 736 |
| | 628 | bt2(2) | 1817 |
| | 305 | bt2(4) | — |
| | 188 | bt2(5) | — |
| | 120 | bt2(1) | — |

FIG. 2*b*—Schematic view of nine bt884 DNA fragments that were inserted into the polylinker of M13 vectors, MP18 and MP19 (Yanisch-Perron et al., 1985). The Bt ICP coding sequence is shown from AUG to 1600 nucleotides downstream. The relevant restriction sites and sizes of the DNA fragments are indicated. The nucleotide numbering is relative to the AUG. The subclones were named pJD71, pJD72, pJD73, etc. (to pJD79), as indicated. The inserts were oriented into the M13 vector such that single stranded M13 carried the fragments of the Bt ICP coding sequence in an antisense orientation.

Figure 2B:
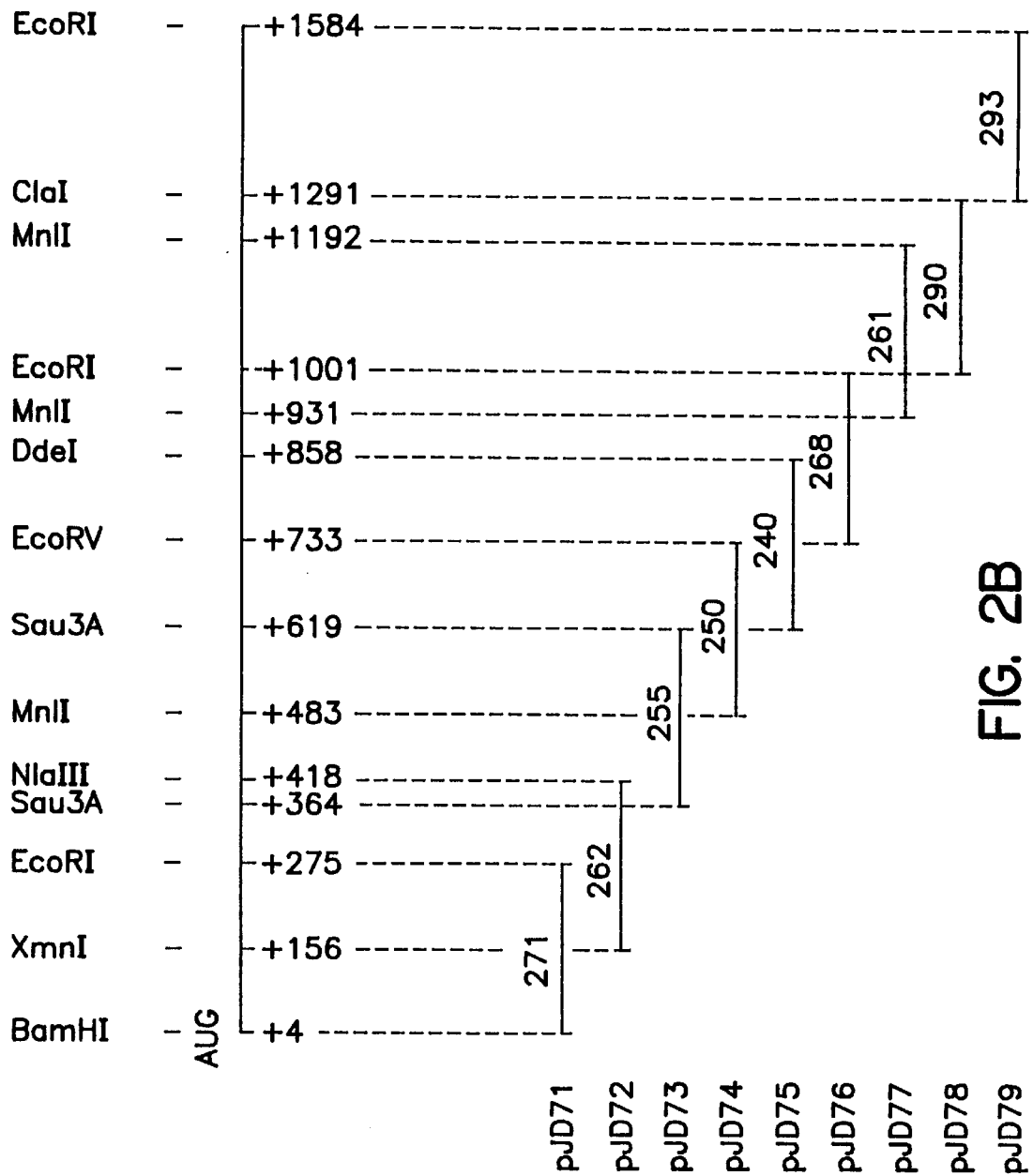
Figure 2C:
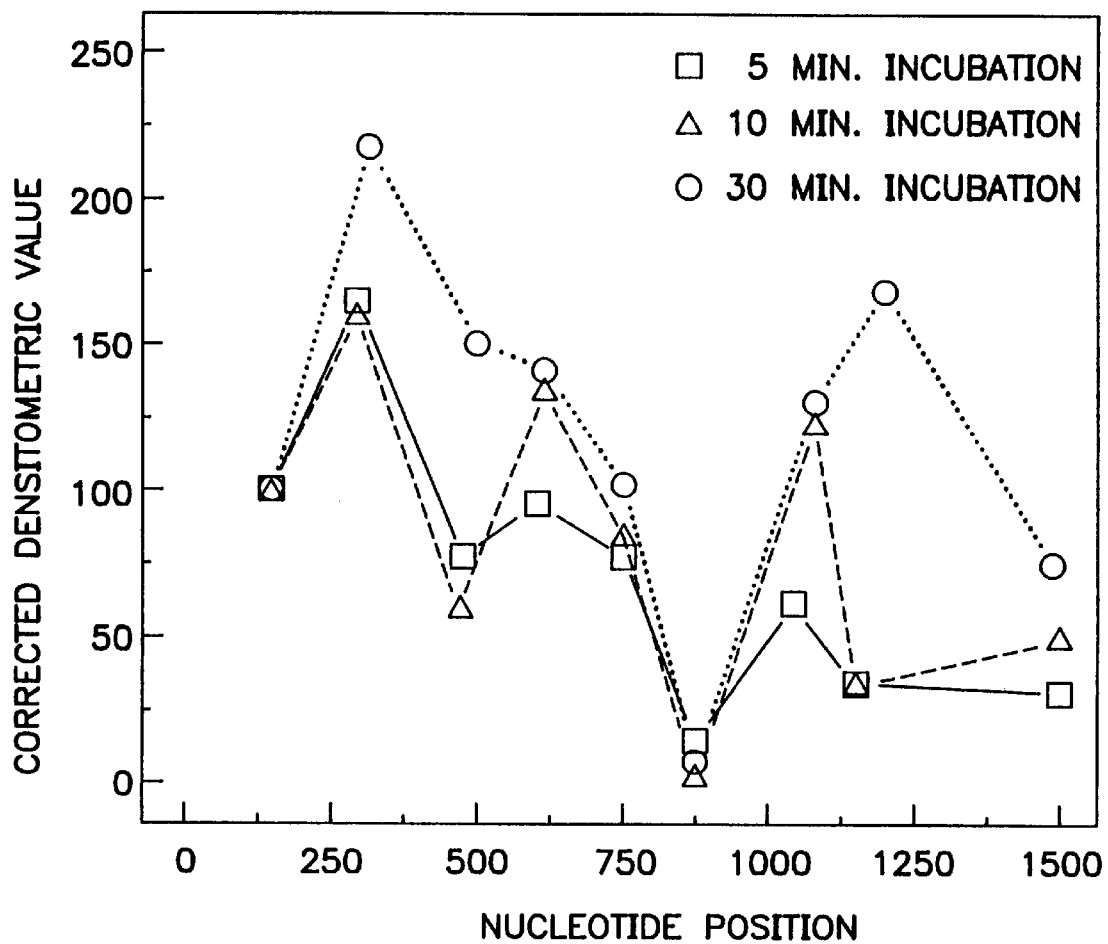

FIG. 2c—Schematic represent

Klenow polymerase I. PJD50was linearized with BamHI and filled in with Klenow polymerase I. The 1021 bp SpeI-XcaI fragment of PVE36 was ligated in the filled in BamHI of pJD50. The ligation mixture was used to transform MC1061 cells. Transformants were selected for amp$^r$ phenotype.

Figure 3A:
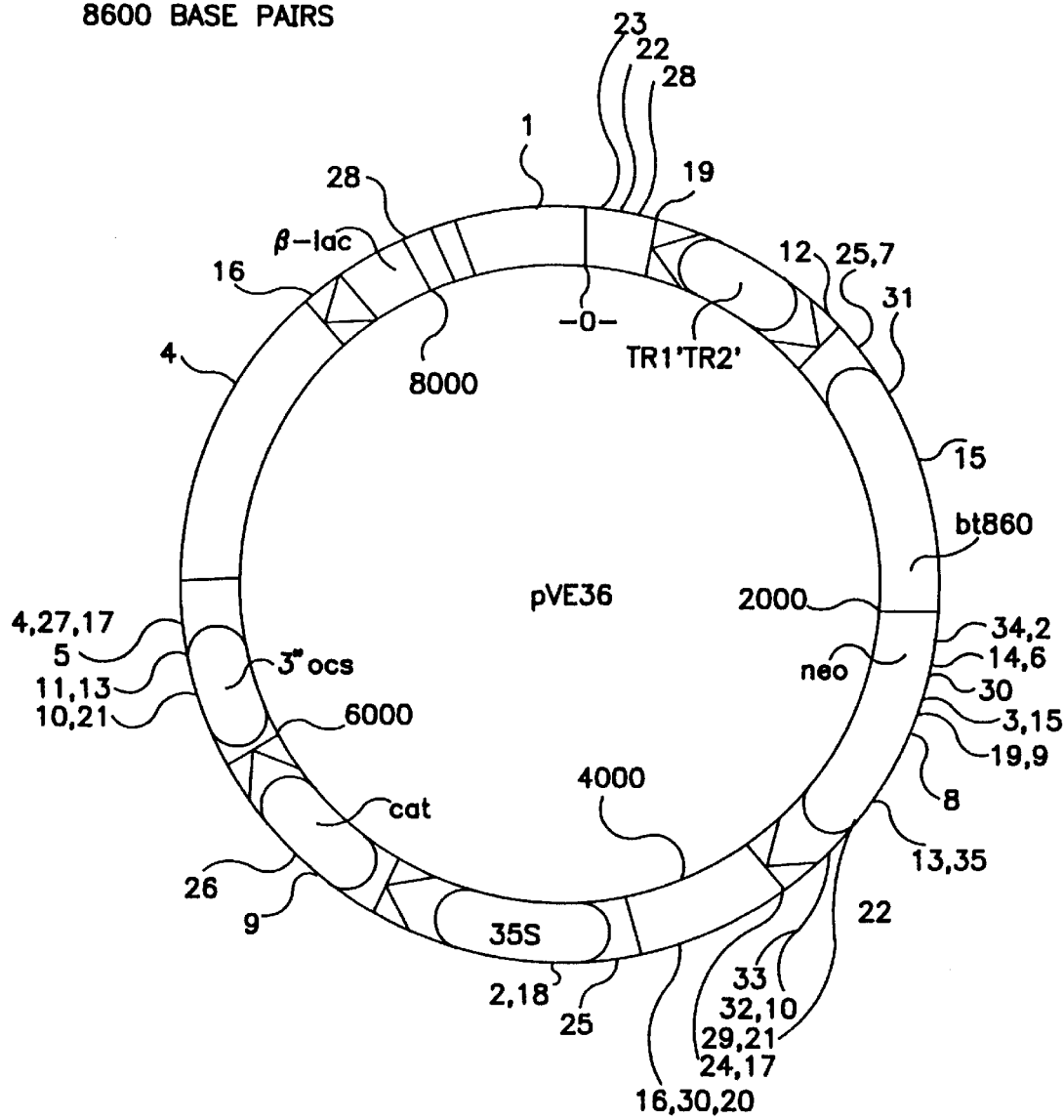
Figure 3B:
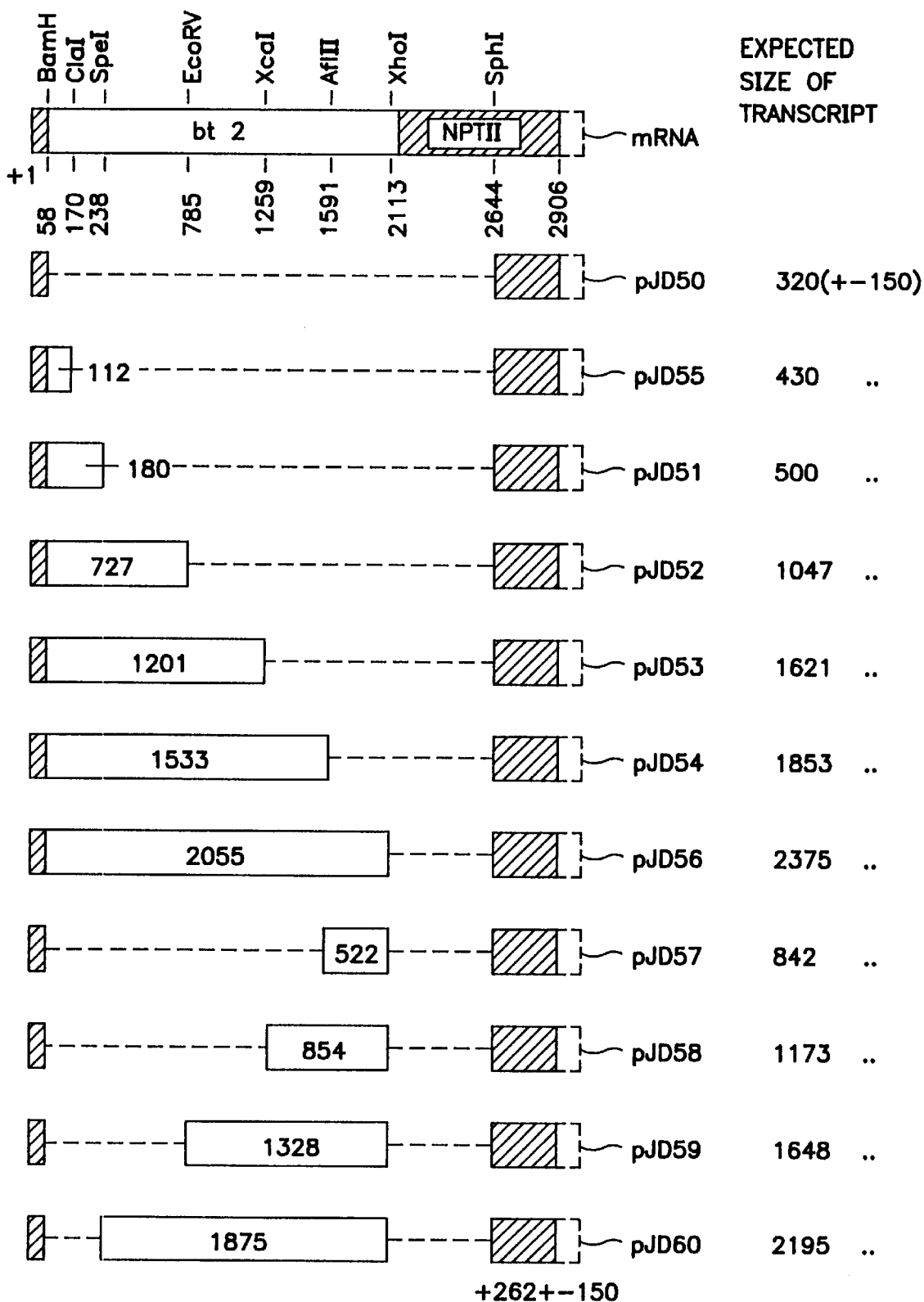
Figure 3C:
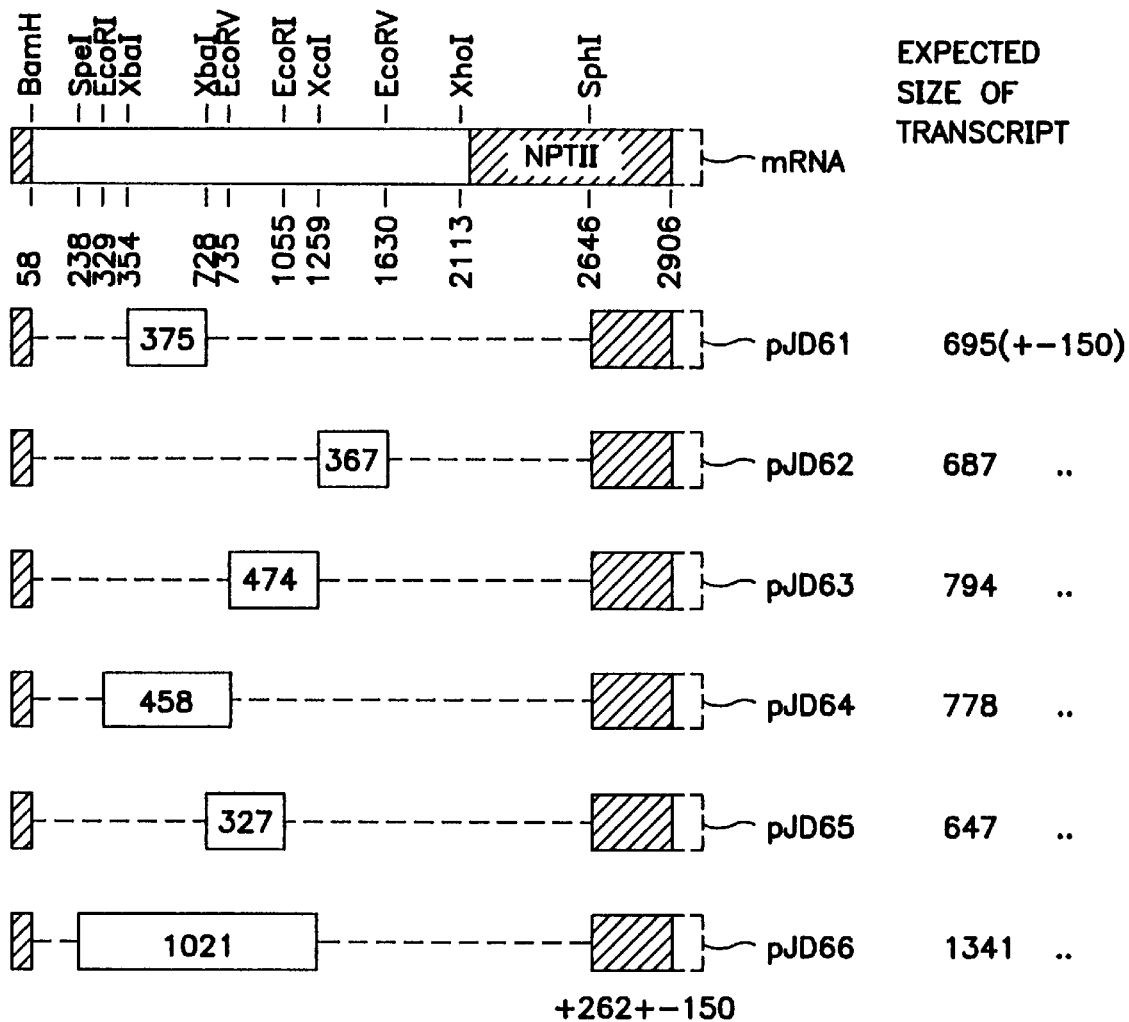
Figure 3D:
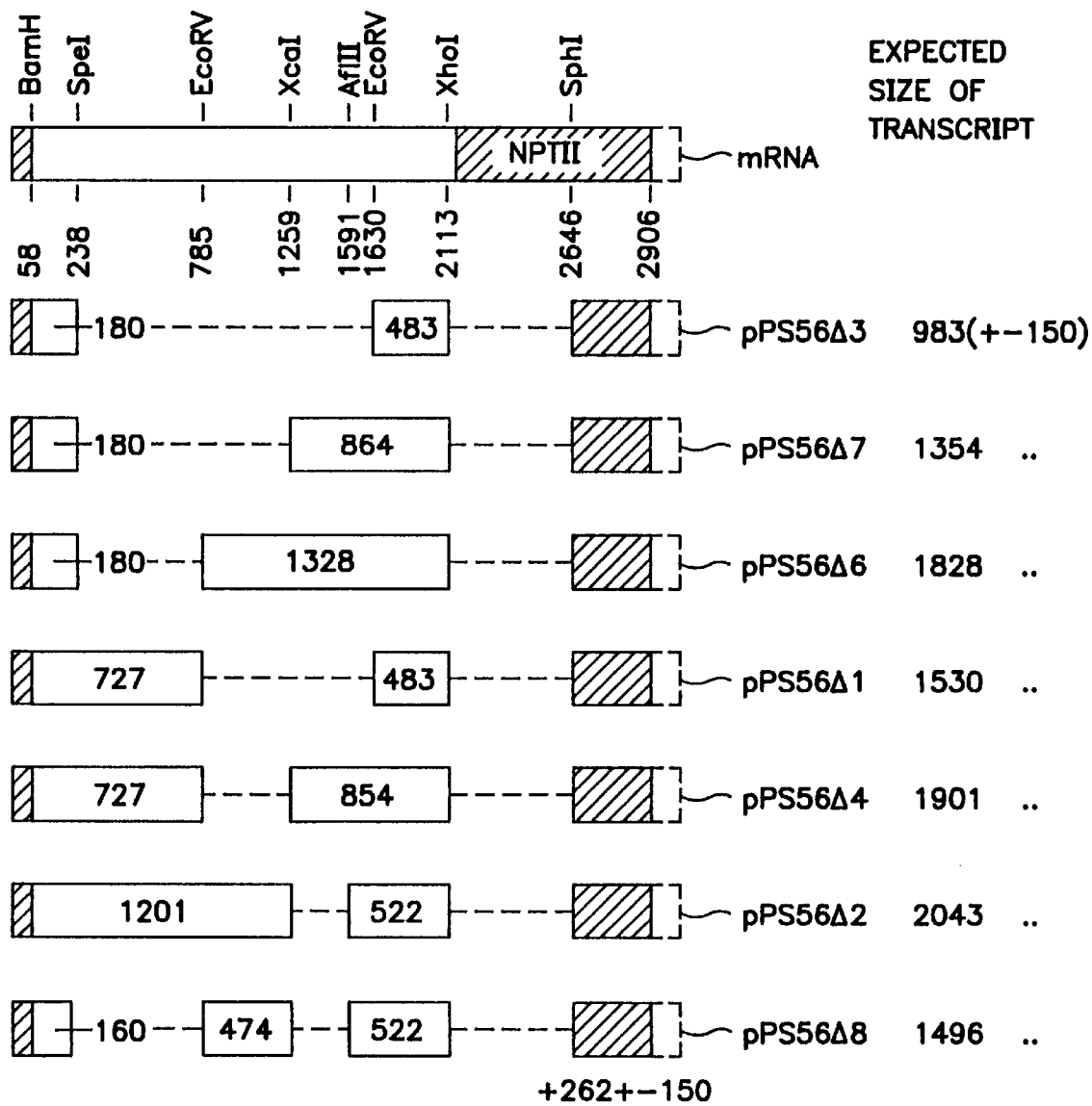
Figure 5:
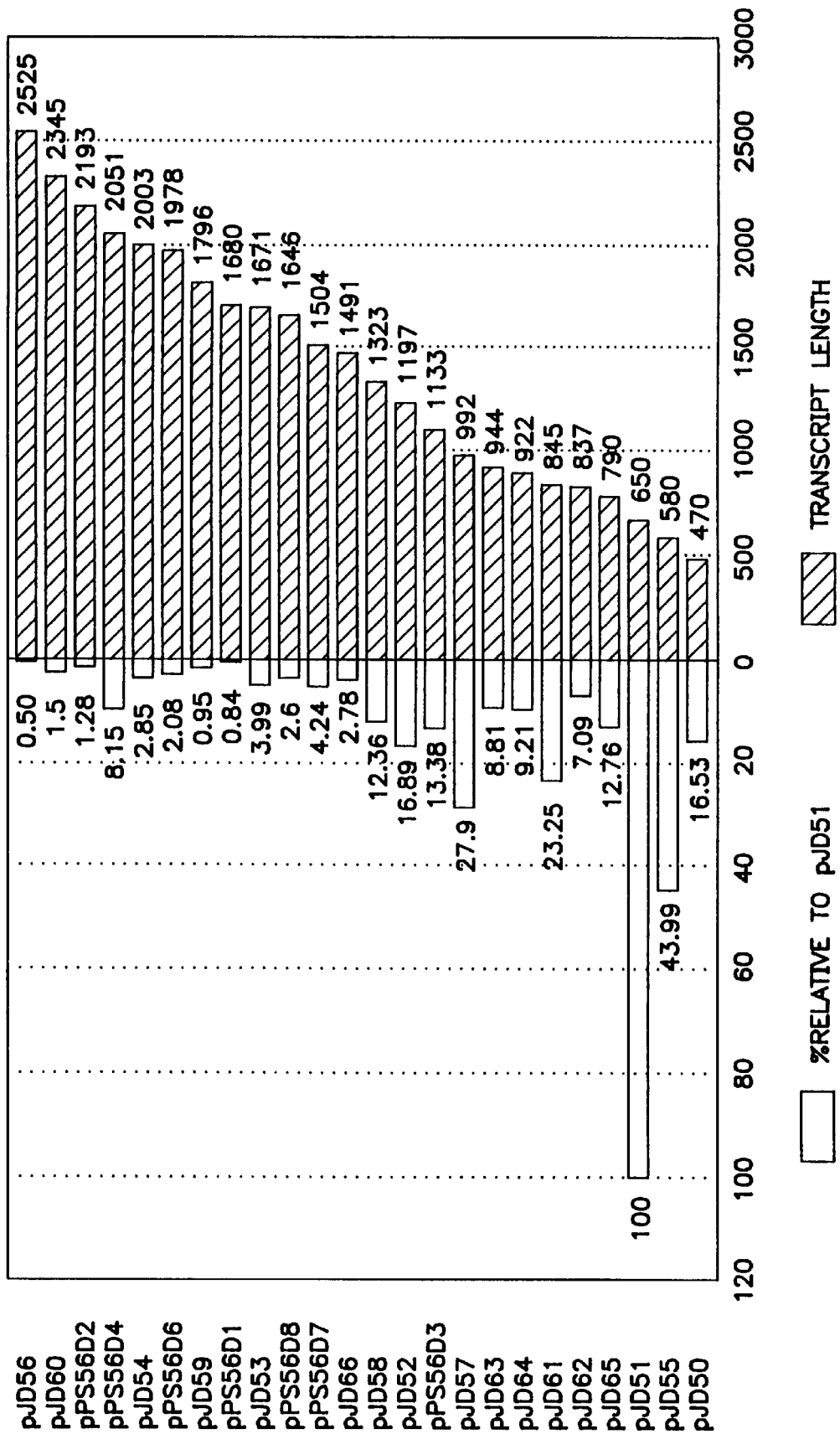

18. PPS56D1 (FIG. 3D): PPS56D1 was derived from PJD56 by digesting with EcoRV. The treated DNA was ligated and then used to transform MC1061 cells. Transformants were selected for amp$^r$ phenotype.

19. PPS56D2 (FIG. 3D): PPS56D2 was derived from PJD56 by digesting with XcaI and AflII. The 5' protruding ends were filled in with Klenow polymerase I. The treated DNA was ligated and then used to transform MC1061 cells. Transformants were selected for amp$^r$ phenotype.

20. PPS56D3 (FIG. 3D): PPS56D3 was derived from PJD56 by digesting with SpeI and EcoRV. The 5' protruding ends were filled in with Klenow polymerase I. The treated DNA was ligated and then used to transform MC1061 cells. Transformants were selected for amp$^r$ phenotype.

21. PPS56D4 (FIG. 3D): PPS56D4 was derived from PJD56 by digesting with XcaI and partially with EcoRV. The treated DNA was ligated and then used to transform MC1061 cells. Transformants were selected for amp$^r$ phenotype.

22. PPS56D6 (FIG. 3D): PPS56D6 was derived from PJD56 by digesting with SpeI and partially with EcoRV. The 5' protruding ends were filled in with Klenow polymerase I. The treated DNA was ligated and then used to transform MC1061 cells. Transformants were selected for amp$^r$ phenotype.

23. PPS56D7 (FIG. 3D): PPS56D7 was derived from PJD56 by digesting with SpeI and XcaI. The 5' protruding ends were filled in with Klenow polymerase I. The treated DNA was ligated and then used to transform MC1061 cells. Transformants were selected for amp$^r$ phenotype.

24. PPS56D8 (FIG. 3D): PPS56D8 was derived from PPS56D2 by digesting with SpeI and partially with EcoRV. The 5' protruding ends were filled in with Klenow polymerase I. The treated DNA was ligated and then used to transform MC1061 cells. Transformants were selected for amp$^r$ phenotype.

Figures 2, 8A:
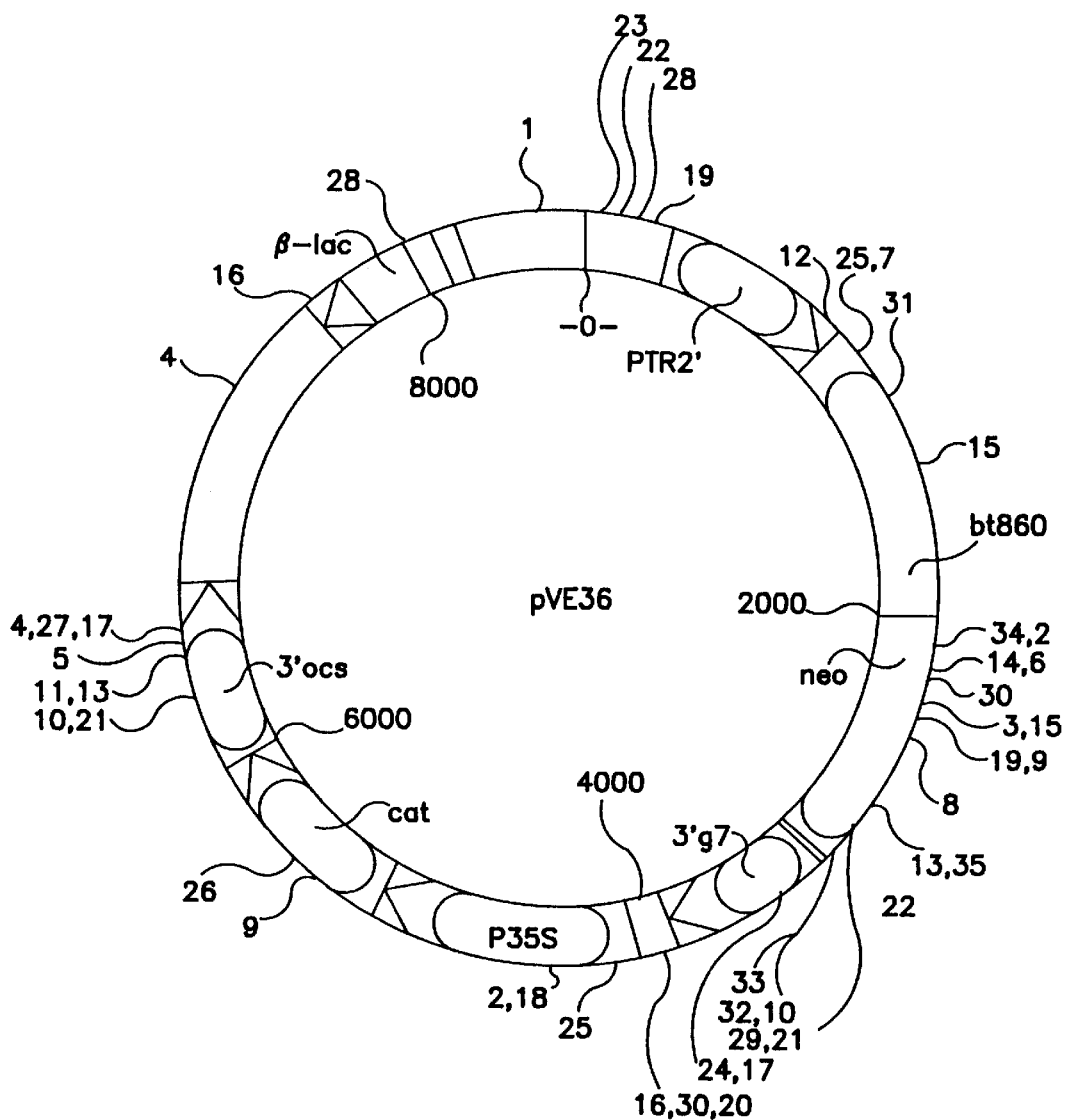
Figures 2, 8B:
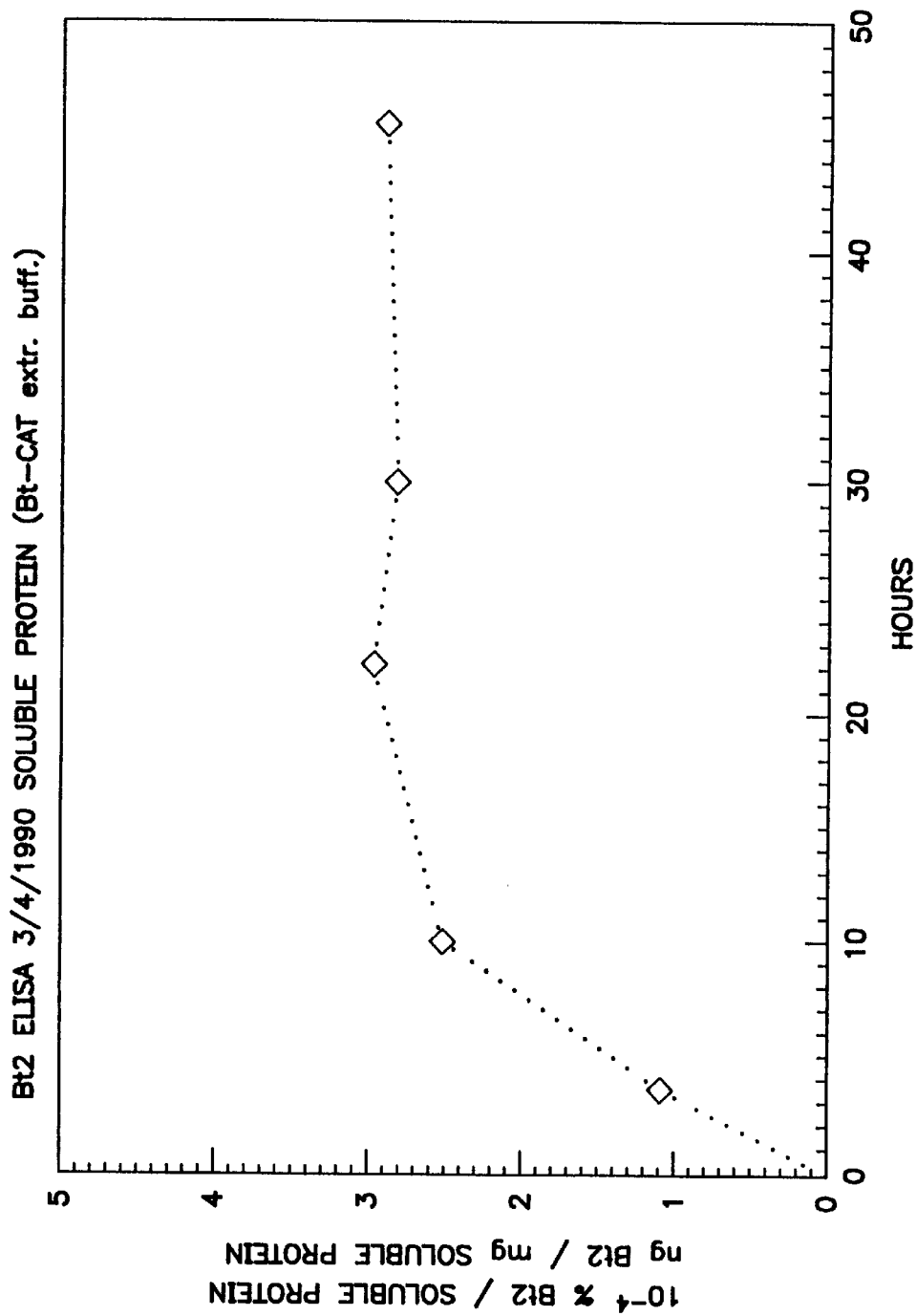
Figures 3, 8B:
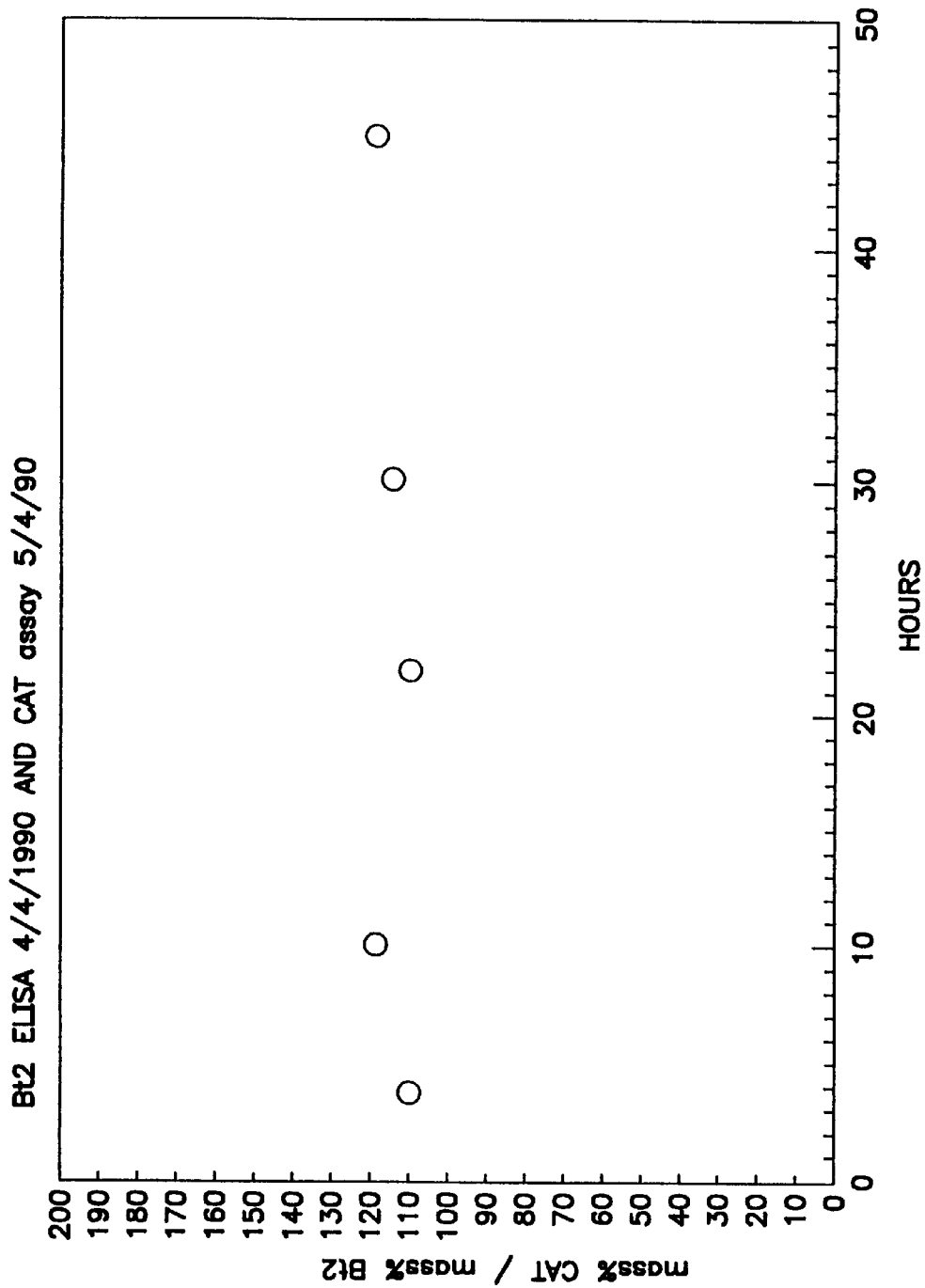

FIG. 4—Effect of deletions in the Bt ICP coding sequence on cytoplasmic Bt ICP mRNA levels. The cytoplasmic mRNA levels specified by the invariable cat reference gene and the different Bt ICP deletion mutants described in FIG. 3 are listed in the table. The measurements were converted into relative Bt ICP mRNA abundances. Bt ICP and cat mRNA quantizations were done as described by Cornelissen (1989). Total RNA was slot blotted and hybridised with radioactively labeled RNA complementary to the neo and cat coding sequences. Values were quantitated with the aid of calibration curves of cold cat and Bt ICP riboprobe transcripts.

FIG. 5—Relative transcript levels produced by the deletion derivatives of pVE36.

FIGS. 6A–6C.—FIG. 6*a*—Schematic presentation of the synthetic DNA sequences used to introduce a N-terminal deletion and a change of the codons 29, 30 and 31 of the bt2 coding sequence. The oligo nucleotides were annealed according to Engler et al. (1988) and cloned into the BstXI restriction site of plasmid pVE36, yielding pPSO27. The 7360 bp fragment of pPSO27was ligated to the the 1177bp ClaI restriction fragment of pVE36, yielding plasmid pPSO28. pPSO28 is identical to pVE36 apart for the N-terminal modification.

FIG. 6*b*—Schematic presentation of the synthetic DNA sequences used to introduce an internal modification into the bt2 coding sequence. The oligonucleotides (FIG. 6B-1) were annealed and ligated (FIG. 6B-2 and 6B-3) as described by Engler et al. (1988) and the resulting concatemeric DNA fragment was cut with the restriction enzymes XbaI and EcoRI to release the modified 327 bp XbaI-EcoRI restriction fragment. This fragment was ligated into the 3530 bp EcoRI-XbaI fragment of pPSO23 which is a pUC19 derivative (Yanisch-Perron et al., 1985) that carries the 1533 bp AflII (filled in) BamHI fragment of pVE36 in the HindIII (filled in) BamHI site of pUC19, resulting in plasmid pPSO24. Plasmid pPSO24 was linearised by digestion with restriction enzyme XbaI and the 375 bp XbaI restriction fragment of pPSO23 was introduced resulting in pPSO25. The 1177 bp ClaI fragment of pPSO25 was introduced in the 7360 bp ClaI restriction fragment of pPSO27 yielding pPSO29. pPSO29 is identical to pVE36 but carries both the amino-terminal modification and the internal modification of the Bt ICP coding sequence.

FIG. 6*c*—Nucleotide sequences 800 to 4000 of the plasmids pVE36 (FIG. 6C-1) and pPSO29 (FIG. 6C-2). "x" refers to not known nucleotides.

FIGS. 7A–7B.—FIG. 7A—Schematic presentation of the effect of the mutations on the AT content of the Bt ICP plant gene. (pVE36: FIG. 7A; pPSO29: FIG. 7B) The modified regions are indicated.

FIGS. 8A–8B—FIGS. 8A-1 and -2—Schematic presentation of the plasmid constructions used in the transient expression assay. The relevant genes are indicated.

FIGS. 8B-1, -2 and -3—Accumulation profiles of CAT (Neumann et al., 1987) and the modified BtICP (Engvall and Pesce, 1978) in a typical transient expression assay.

DETAILED DESCRIPTION OF THE INVENTION

Unless otherwise stated in the Examples, all procedures for making and manipulating recombinant DNA are carried out by the standardized procedures described in Sambrook et al., *Molecular Cloning—A laboratory Manual*, Cold Spring Harbor Laboratory (1989).

EXAMPLES

Example 1

Determination of the Efficiency of Transcription Initiation

The relative efficiency of RNA polymerase II complexes to initiate transcription at chimaeric BtICP plant genes was studied, using transgenic plant N28–220 which is described by Vaeck et al. (1987) and contains copies of the T-DNA of plasmid pGSH163 This T-DNA carries the chimaeric plant genes $P_{TR2}$bt8843'g7 and $P_{TR1'}$neo3'ocs. Nuclei of 25 g of induced leaves of N28–220 were prepared according to Cox and Goldberg (1988) and stored the nuclei at a temperature of −70° C. This method causes the nascent precursor mRNA chains and the RNA polymerase II complexes to halt while the complexes remain associated at the DNA. A batch of these nuclei was assayed for the ability to incorporate radioactively labeled UTP as a measure for the transcriptional viability of the nuclei (Cox and Goldberg (1988). This incorporation could be successfully repressed by addition of α-amanitin to a final concentration of 2 μg/ml. This shows that the UTP incorporation was due to transcript elongation by RNA polymerase II and that RNA synthesis on the protein coding genes which are occupied by RNA polymerase II can be reactivated under the appropriate experimental conditions.

Batches of the nuclei of N28–220 were used to synthesize radioactively labeled RNA as described by Cox and Goldberg (1988). The radioactive RNA synthesized is a direct representation of the distribution of the RNA polymerases II complexes on the DNA in the nuclei. As the DNA of N28–220 carries two genes which can be assayed, namely the chimaeric neo gene and the chimaeric Bt ICP gene, it is possible to compare the distribution of RNA polymerase II complexes on these two genes. To this end, the radioactive RNA was extracted from the nuclei according to Cox and Goldberg (1988) and used as a probe in a conventional Southern hybridisation. The Southern blot contained DNA fragments carrying the Bt ICP and neo coding sequences in a molar excess relative to the neo and Bt ICP RNA species present in the radioactive probe. A detailed description of the Southern blot is given in FIG. 1. The hybridisation experiment resulted in hybridisation signals to both the neo and Bt ICP coding sequences (FIG. 1). Densitometric scanning showed that the intensity of the hybridisation signal to the neo and Bt ICP coding regions was nearly identical. This result implies that the number of transcripts initiating from the TR dual promoter is about similar in both directions. As in plant N28–220 the cytoplasmic neo mRNA level is several magnitudes higher than that of Bt ICP; this shows that the Bt ICP coding sequence indeed negatively controls accumulation of cytoplasmic Bt ICP mRNA, but that this phenomenon is not due to a dominant negative effect on transcription initiation of the chimaeric Bt ICP plant gene.

Example 2

Transcription Elongation

The relative distribution of RNA polymerase II complexes on the Bt ICP plant genes present in transgenic plant N28–220 which is described by Vaeck et al. (1987) was investigated. To this end, a second experiment was carried out with batches of the nuclei of N28–220 described in Example 1.

The nuclei were incubated as described by Cox and Goldberg (1988) to synthesize radioactively labeled RNA. The radioactive RNA was extracted as described previously to provide a probe for a Southern hybridisation. The Southern blot prepared for this experiment contained several fragments of the Bt ICP coding sequence in molar excess relative to the complementary RNA present in the probe. The rationale of the experiment was that if the RNA polymerase II complexes were equally distributed over the Bt ICP coding region, the hybridisation with the different Bt ICP DNA fragments present on the Southern blot would be proportional to the size and DATP content of the different fragments. A detailed description of the DNA fragments present on the Southern is given in FIG. 2*a*. The hybridisation of the radioactive RNA extracted from the nuclei of N28–220 with the Southern revealed that the complete Bt ICP coding sequence as present in N28–220 is transcribed by RNA polymerase II.

Quantification of the hybridisation signals by densitometric scanning of the autoradiogram showed that more radioactively labeled RNA was hybridising with DNA fragments representing Bt ICP sequences located 5' on the Bt ICP coding sequence than with Bt ICP sequences located 3' on the Bt ICP coding sequence. The actual values are given in FIG. 2*a*. This in vitro experiment demonstrates that in vivo the RNA polymerases are not evenly distributed over the Bt ICP coding sequence.

The site(s) involved in reducing the RNA polymerase II elongation were then determined more accurately. Nine M13 derivatives were made that carry overlapping fragments of the Bt2 coding sequence spanning the region from the AUG to 1584 nucleotides downstream. The inserts were oriented into the vector such that, in single stranded M13 derivatives, the Bt sequences were complementary to the Bt transcript. A schematic view of the M13 clones is given in FIG. 2*b*.

A molar excess of each single stranded anti-Bt DNA was bound to nylon filters to serve as a DNA target for hybridisation with labeled RNA prepared from nuclear run-on assays with N28–220 nuclei as described by Cox and Goldberg (1988). Three nuclear run-ons that differed only in their time period of incubation were carried out simultaneously. The incubation time determines the length of extension of the nascent mRNA chain. Shorter incubation periods give a more accurate view of the position of the RNA polymerase II complexes relative to the substrate DNA and their ability to elongate at the moment of the start of incubation. Hence, the shorter the in vitro incubation period, the more accurate the view in predicting the in vivo situation.

The results are shown in FIG. 2*c*. The data for the minute incubation show that, in vivo, at a very discrete inhibitory zone along the bt2 coding sequence, one or more factors interfere with transcript elongation and that such factor(s) remain present in such inhibitory zone during the course of the in vitro mRNA extension reaction. Increased incubation periods show that, on a subset of DNA templates, RNA synthesis resumed downstream of such inhibitory zone in this assay without significantly removing the inhibition in the inhibitory zone itself. In this regard, the data indicate that:

1. The inhibitory zone causes the RNA polymerases to pause and not to terminate.
2. This pause is only transitory for a small fraction of the Bt DNA templates which were used.
3. The continued RNA polymerase elongation, downstream of the inhibitory zone, is done by a large number of polymerases on the relatively small fraction of the Bt DNA templates.

It is believed, therefore, that low cytoplasmic Bt mRNA levels are due at least in part to inefficient production of precursor mRNA caused by inefficient elongation of a nascent transcript and/or stalling of RNA polymerase II complexes from transcribing at an inhibitory zone.

The inhibitory zone was assayed for its ability to interact with proteins present in nuclei of tobacco protoplasts. A crude nuclear extract was prepared from tobacco SR1 leaf protoplasts according to Luthe and Quatrano (1980) and used for filter binding assay essentially as described by Diffley and Stillman (1986). 100 ng samples of protein extract were mixed with different amounts of radioactively labeled 532 bp XbaI-AccI bt884 DNA fragment, ranging from 0 to 1670 picomolar, in a final volume of 0.150 ml binding buffer (10 mM Tris pH 7.5, 50 mM NaCl, 1 mM DTT, 1 mM EDTA and 5% glycerol). After 45 minutes incubation at room temperature, the samples were filtered through an alkali-washed nitrocellulose membrane and washed twice with 0.150 ml of an ice-cold solution containing 10 mM Tris pH 7.5, 50 mM NaCl and 1 mM EDTA. The retention of DNA-protein complex was quantified by scintillation counting and revealed that the binding had a dissociation constant in the 100 picomolar range. The binding was not affected by preincubation of the nuclear extract with a molecular excess of a specific competitor DNA.

Example 3

Construction of Deletion Mutants

The previous two examples demonstrate that the Bt ICP coding sequence in a chimaeric plant gene negatively affects the cytoplasmic Bt ICP mRNA level directed by the chimaeric plant gene. It is shown that this negative control is not at the level of transcription initiation but at least in part due to a reduced ability of RNA polymerase II to generate precursor Bt ICP mRNA. A deletion analysis of the chimaeric Bt ICP plant gene was performed to identify whether impaired transcription elongation is the exclusive mechanism by which the Bt ICP sequence interferes with gene expression. The rationale of the experiment is that the introduction of specific deletions in the Bt ICP coding region could remove or inactivate the sequence element(s) responsible for the negative control. As a result such mutant gene would direct an increased level of cytoplasmic mRNA. This method can therefore be used to map and identify the sequence(s) involved in the negative control.

To perform this analysis, a deletion series of the bt860-neo gene (Vaeck et al., 1987) was made. FIG. 3 gives a schematic representation. The resultant deletion derivatives do not specify a Bt ICP and therefore are assayed at RNA level only. In order to obtain accurate Bt ICP mRNA concentration values, the deletion mutants were compared in a transient expression system using tobacco leaf protoplasts of SR1 (Cornelissen and Vandewiele, 1989). The relative mRNA abundances were calculated using a correction factor provided by the mRNA level specified by the cat reference gene present on the same plasmid as the mutant Bt ICP gene. Four hours after introduction of the genes the tobacco leaf protoplasts were harvested, and total RNA was prepared and analysed (FIG. 4).

The mutants nos. 50–60 (FIG. 3) show that progressive deletions of the carboxy-terminal part or the amino-terminal part of the Bt ICP coding sequence result in a gradually increasing neo transcript level. As there are not very abrupt changes in transcript levels, these results suggest that the low transcript level produced by full length Bt ICP genes is controlled by a number of signals. Deletions within the Bt ICP coding sequence indeed did not localise a specific sequence element which, by itself, is responsible for the low Bt ICP mRNA level. Similarly, cloning of fragments of the Bt ICP coding sequence in pJD50 (FIG. 3) did not allow identification of such a region.

The relative transcript levels were plotted against the length of the Bt ICP sequence present in the different deletion derivatives. FIG. 5 suggests that hybrid Bt ICP-neo transcript levels drop with increasing length of the Bt ICP sequence. In this respect, the mutants nos. 61–66 (FIG. 3) form an exception as they show in average a low transcript level relative to the length of the Bt ICP sequence.

These results show that the low transcript levels of Bt ICP plant genes in tobacco are not exclusively due to an impaired elongation of the nascent transcript but that a number of signals operate to cause a reduced expression capacity of the chimaeric Bt ICP gene.

Example 4

To determine whether cytoplasmic events are important in causing inefficient expression of the bt2 gene in plants, the following test was carried out. Cytoplasmic bt2 mRNA steady state levels in transgenic leaf protoplasts of N28–220 are normally found to be below 1 transcript per cell. The steady state level is determined by, and is proportional to, the number of bt2 transcripts entering per time unit the cytoplasm and the cytoplasmic half-life of the transcript. When steady state levels are achieved, the absolute numbers of transcripts entering and leaving the cytoplasmic bt2 mRNA pool are equal. Therefore, the cytoplasmic half-life and cytoplasmic steady state level of the bt2 transcript will reveal whether its cytoplasmic steady state level is due to a relatively low import of bt2 transcript, a relatively high turnover (i.e., conversion to a protein) rate, or a combination of both.

The cytoplasmic turnover of bt884 transcripts was determined according to Gallie et al. (1989). A capped and polyadenylated synthetic bt884 mRNA was produced in vitro according to protocols of Promega Corporation (Madison, Wis., USA) and introduced into tobacco leaf protoplasts simultaneously with a synthetic bar (De Block et al., 1987) mRNA. The two synthetic transcripts differed only in their coding sequences. At various times after RNA delivery, samples were taken, and total RNA was isolated. Northern analyses revealed that the half-lives (T ½) of the synthetic bt884 and bar transcripts were about 8±3 hours and 5±2 hours, respectively. See Table 1, below. These data show that the bt884 coding sequence, more particularly the bt884 codon usage and the AU-rich motifs in the bt884 coding sequence, do not render the bt884 mRNA more unstable than the bar mRNA which is known to accumulate in the cytoplasm to about 1000 transcripts per tobacco leaf protoplast (calculated from Cornelissen, 1989). The low cytoplasmic steady state level of the bt884 transcripts is, therefore, caused by a lack of import of transcripts into the cytoplasm. Thus, the expression defect of the bt884 gene has to be restored by introduction of modifications in the bt884 coding sequence that improve the expression pathway in the nucleus.

Expression of the bt14, bt15 and bt18 genes in tobacco revealed that these genes also direct low cytoplasmic mRNA steady state levels. Therefore, a similar analysis was carried out with synthetic bt14, bt15 and bt18 transcripts to identify whether the expression defect had a cytoplasmic or nuclear character. Table 1, below, shows that all three transcripts behave as stable mRNAs in the cytoplasm of tobacco leaf protoplasts. Therefore, bt14, bt15 and bt18 genes, like the bt884 gene, must be deficient in exporting high levels of bt transcript to the cytoplasm, and to improve the expression of such genes, it is necessary to modify their coding sequences so that nuclear events, which interfere with efficient gene expression, are avoided or ameliorated.

TABLE 1

Half-life determination of synthetic bt and bar mRNAs in *Nicotiana tabacum* cv. Petite Havanna SR1 leaf protoplasts

| Example | 1st mRNA | T½ (Hours) | 2nd mRNA | T½ (Hours) |
|---|---|---|---|---|
| A | bt884 | 8 +/− 3 | bar | 5 +/− 2 |
| B | bt14 | 7 +/− 2 | bar | 6 +/− 3 |
| C | bt15 | 12 +/− 5 | bar | 21 +/− 12 |
| D | bt18 | 10 +/− 5 | bar | 12 +/− 5 |

Legend

The synthetic bar transcripts had a length of 783 bases and included a cap, the TMV leader (77 bases, Danthinne and Van Emmelo, 1990), the bar coding sequence (552 bases; De Block et al., 1987), a trailer of 52 nucleotides consisting of the bases GAUCA CGCGA AUU and 39 bases from the pGEM-3Z (Promega) polylinker (KpnI (T4 DNA pol.)-

HindIII (T4 DNA pol.), and a poly(A) of the composition $(A)_{33}G(A)_{32}G(A)_{32}$, followed by the nucleotides GCU.

The synthetic bt884 transcripts had a length of 2066 bases and included a cap, the TMV leader (77 bases), the bt884 coding sequence followed by the trailer until the Klenow treated PstI site (1843 nucleotides), the trailer continued with AAUUC CGGGG AUCAA UU, 39 bases of the pGEM-3Z polylinker and the $(A)_{33}G(A)_{32}G(A)_{21}$ poly(A), followed by the nucleotides CG.

The synthetic bt14 transcripts had a length of 2289 bases and included a cap, the TMV leader (77 bases), the bt14 coding sequence till the Klenow treated BclI site (2023 bases), plus 26 supplementary nucleotides CG UCG ACC UGC AGC CAA GCU UGC UGA, a trailer starting with UUGAU UGACC GGAUC CGGCU CUAGA AUU, followed by 39 bases of the pGEM-3Z polylinker, and the $(A)_{33}G(A)_{32}G(A)_{21}$ poly(A), followed by the nucleotides CGGUA CCC.

The synthetic bt15 transcripts had a length of 2198 bases and included a cap, the TMV leader (77 bases) the bt15 coding sequence as in pVE35 (PCT publication WO90/15139) followed by the trailer till the Klenow treated BamHI site (1989bases), the trailer then continued with AAUU, 39 bases of the pGEM-3Z polylinker and the $(A)_{33}G(A)_{32}G(A)_{21}$ poly(A), followed by the nucleotides CG.

The synthetic bt18 transcripts had a length of 2184 bases and included a cap, the TMV leader (77 bases) the bt18 coding sequence until the Klenow treated BcLI site (1918 bases), followed by 26 nucleotides until the translation stop CG UCG ACC UGC AGC CAA GCU UGC UGA, a trailer starting with UUGAU UGACC GGAUC GAUCC GGCUC AGAUC AAUU, 39 bases of the pGEM-3Z polylinker and the $(A)_{33}G(A)_{32}G(A)_{21}$ poly(A), followed by the nucleotides CG.

Example 5

Construction of Modified Bt ICP Genes

Examples 1–4 show that the expression in a plant of a Bt ICP gene is negatively affected by the Bt ICP coding sequence at both transcriptional and post-transcriptional levels, but principally by nuclear events. These examples also show that the control of expression is not confined to a specific DNA sequence within the Bt ICP coding sequence. Instead, the negative effect on gene expression is an intrinsic property of the Bt ICP coding sequence. On this basis, it is believed that, by directed change of the DNA sequence of the Bt ICP coding region, an improvement of gene expression will occur. The improvement will be of a cumulative type as the negative influence of the Bt ICP coding region is spread over the complete coding sequence. Similarly, an improvement of gene expression will be obtained by reduction of the length of the Bt ICP coding sequence. This improvement will have a cumulative effect if used in combination with modifications of the Bt ICP coding region.

Figure 7A:
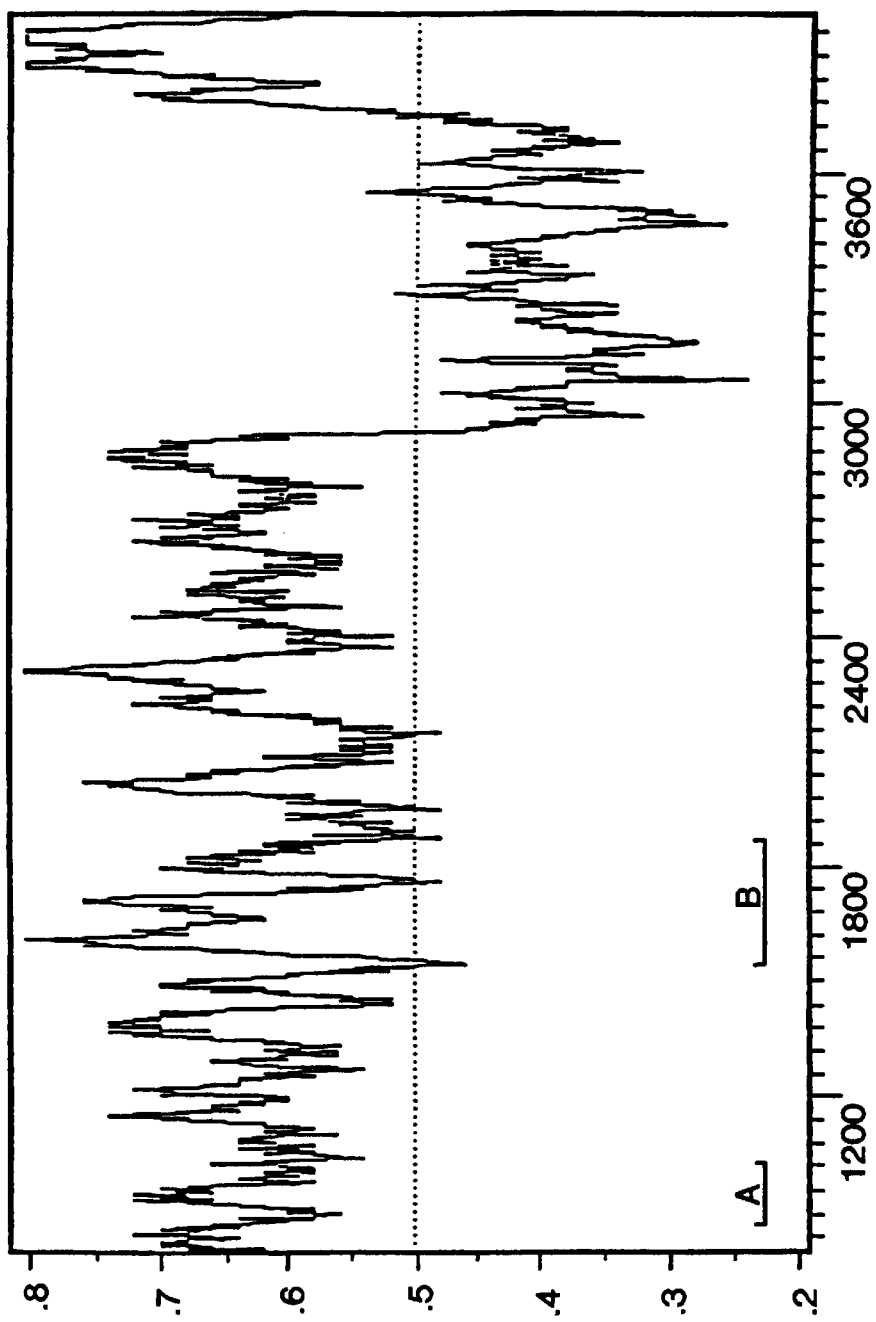
Figure 7B:
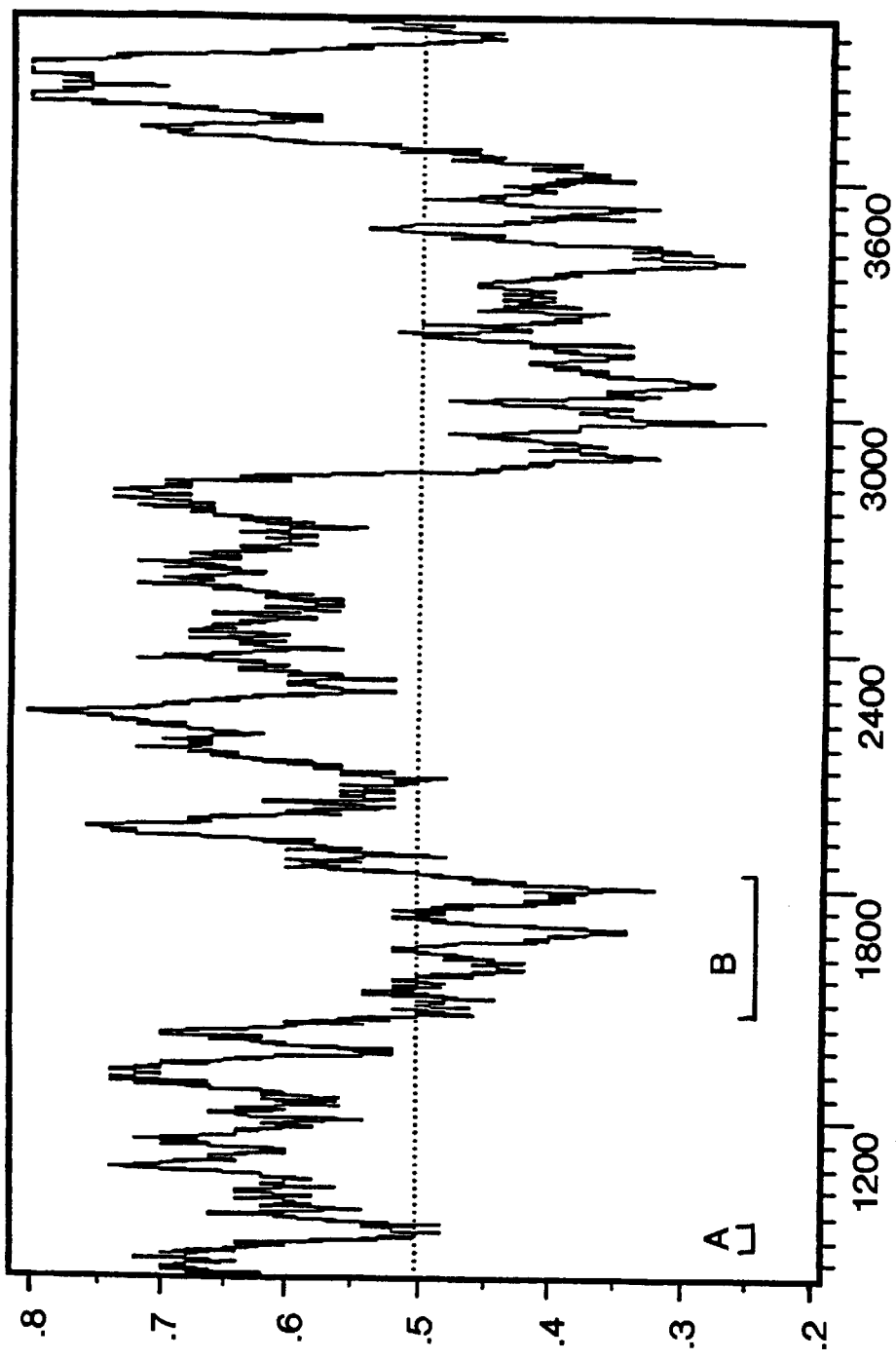

Therefore, two types of modifications were introduced into a Bt ICP (i.e., bt2) coding sequence which, as will be shown, indeed resulted in a significant increase in Bt ICP plant gene expression. First, the DNA sequence was modified in the central region of the toxic core fragment of the Bt ICP as transcription elongation is impaired in this region. Secondly, the length of the Bt ICP coding sequence was reduced as the negative influence is proportional to the length of the Bt ICP coding sequence. A detailed description of the mutations is given in FIGS. 6a, b and c. As shown in FIG. 7, the modifications change the AT-content of the chimaeric Bt ICP gene significantly. The modifications change the primary DNA structure of the Bt ICP coding sequence without affecting the amino acid sequence of the encoded protein. It is evident that, if more DNA mutations were to be introduced into the Bt ICP coding sequence, a further improvement of gene expression would be obtained.

To determine the effect of the modifications, the expression properties of the modified BtICP gene and the parental bt860-neo gene were compared in a transient expression system as described by Cornelissen and Vandewiele (1989) and Denecke et al. (1989). Basically, the accumulation profiles of the genes under study were compared by relating their profiles to the profile of a reference gene present in the same experiment. FIG. 8a shows the vectors used in the assay, and FIG. 8b shows that the accumulation of the reference CAT protein is nearly identical in both experiments. It is not possible to measure the accumulation of Bt ICP encoded by the parental bt860-neo gene, but the modified Bt ICP gene clearly directs an increased synthesis of Bt ICP.

These results demonstrate that mutation of the Bt ICP coding sequence relieves the negative influence of the Bt ICP coding sequence on the expression of a Bt ICP plant gene.

Example 6

Cloning and Expression of Modified BT ICP Genes in Tobacco and Potato Plants Using the procedures described in U.S. patent application Ser. No. 821,582, filed Jan. 22, 1986, and EPA 86300291.1, EPA 88402115.5 and EPA 89400428.2, the modified Bt ICP (i.e., bt2) genes of FIGS. 6 and 7 are inserted into the intermediate T-DNA vector, pGSH1160 (Deblaere et al., 1988) between the vector's T-DNA terminal border repeat sequences.

To obtain significant expression in plants, the modified Bt ICP genes are placed under the control of the strong TR2' promoter (Velten et al., 1984) and are fused to the transcript 3' end formation and polyadenylation signals of the T-DNA gene 7 (Velten and Schell, 1985).

In addition, the translation initiation context or site are changed in accordance with the Joshi consensus sequence (Joshi, 1987) in order to optimize the translation initiation in plant cells. To this end, an oligo duplex (FIGS. 6a and 6b) is introduced to create the following sequence at translation initiation site: AAAACCATGGCT. In this way, an additional codon (i.e., GCT) coding for alanine is introduced. Additionally, KpnI and BstXI sites are created upstream of the ATG translation initiation codon.

Using standard procedures (Deblaere et al., 1985), the intermediate plant expression vectors, containing the modified BtICP gene, are transferred into the Agrobacterium strain C58C1 Rif$^R$ (U.S. patent application Ser. No. 821,582; EPA 86300291.1) carrying the disarmed Ti-plasmid pGV2260 (Vaeck et al., 1987). Selection for spectinomycin resistance yields cointegrated plasmids, consisting of pGV2260 and the respective intermediate plant expression vectors. Each of these recombinant Agrobacterium strains is then used to transform different tobacco plant cells (*Nicotiania tabacum*) and potato plant cells (*Solanum tuberosum*) so that the modified Bt ICP genes are contained in, and expressed by, different tobacco and potato plant cells.

The transgenic tobacco plants containing the modified Bt ICP genes are analyzed with an ELISA assay. These plants are characterized by a significant increase in levels of Bt (Bt2) proteins, compared to a transgenic tobacco plant containing a non-modified Bt ICP (bt2) gene.

The insecticidal activity of the expression products of the modified Bt ICP (bt2) genes in leaves of transformed tobacco and potato plants is evaluated by recording the growth rate and mortality of larvae of Tobacco hornworm (*Manduca sexta*), Tobacco budworm (*Heliotis virescens*) and potato tubermoth (*Phthorimaea operculella*) fed on leaves of these two types of plants. These results are compared with the growth rate of larvae fed leaves from tobacco and potato plants transformed with the unmodified or parental Bt ICP (bt2) gene and from untransformed potato and tobacco plants. Toxicity assays are performed as described in EPA 88402115.5 and EPA 86300291.1.

A significantly higher mortality rate is obtained among larvae fed on leaves of transformed plants containing and expressing the modified Bt ICP genes. Tobacco and potato plants containing the modified Bt ICP genes show considerably higher expression levels of Bt ICPs compared to tobacco and potato plants containing the unmodified Bt ICP gene.

The insecticidal activity of three transgenic tobacco plants containing the modified Bt ICP genes is determined against second and third instar larvae of *Heliothis virescens*. The control plant was not transformed. The results are summarized in Table 2, below.

TABLE 2

| Plant | % mortality of insects (recorded after 5 days) |
|---|---|
| Control | 11 |
| No. 1 | 100 |
| No. 2 | 88.5 |
| No. 3 | 100 |

Needless to say, this invention is not limited to tobacco and potato plants transformed with the modified Bt ICP gene. It includes any plant, such as tomato, alfalfa, sunflowers, corn, cotton, soybean, sugar beets, rapeseed, brassicas and other vegetables, transformed with the modified Bt ICP gene.

Nor is the invention limited to the use of *Aarobacterium tumefaciens* Ti-plasmids for transforming plant cells with a modified Bt ICP gene. Other known techniques for plant transformation, such as by means of liposomes, by electroporation or by vector systems based on plant viruses or pollen, can be used for transforming monocotyledonons and dicotyledons with such a modified Bt ICP gene.

Nor is the invention limited to the bt2 gene, but rather encompasses all Cry I, Cry II, CryIII and Cry IV Bt ICP genes.

REFERENCES

Adang et al., Gene 36, 289–300 (1985).
Asselin et al., Oncogene 4, 549–558 (1989).
Barton et al., Plant Physiol. 85, 1103–1109 (1987).
Connely and Manley, Cell 57, 567–571 (1989)
Connely and Manley, Molecular and Cellular Biology, 9, 5254–5259 (1989)
Cornelissen, Nucl. Acids Res. 17, 7203–7209 (1989).
Cornelissen and Vandewiele, Nucl. Acids Res. 17, 833–843 (1989).
Cox and Goldberg, in: Plant Molecular Biology, A practical approach, edited by C. Shaw, IRL Press, pp.1–35 (1988).
Danthinne and Van Emmelo, Me. Fac. Landbouww. Rijksuniv. Gent 55 (3a), 1037–1045 (1990).
Darnell, Nature 297, 365–371 (1982).
Deblaere et al., Methods in Enzymology 153, 277–292 (1988).
Deblaere et al., Nucleic Acids Research 13, 4777–4787 (1985).
De Block et al., EMBO J. 6, 2513–2518 (1987).
Delannay et al., Bio/Technology 7, 1265–1269 (1989).
Denecke et al., Meth. Mol. Cel. Biol. 1, 19–27 (1989).
Diffley and Stillman, Mol. and Cell. Biol. 6, 1363–1373 (1986).
Dulmage H. T, "Production of Bacteria for Biological Control of Insects" in "Biological Control in Crop Production" Ed. Paparizas D. C., Osmum Publishers, Totowa, N.Y., USA, pp. 129–141 (1981).
Engler et al., J. Biol. Chem. 263, 12384–12390 (1988).
Engvall and Pesce, Scand. Immunol. Suppl. 7 (1978).
Fischoff et al., Bio/Technology 5, 807–812 (1987).
Fromm et al., Bio/Technology 8, 833 et seq. (1990).
Gallie et al., Plant Cell 1, 301–311 (1989).
Gasser and Fraley, Science 244, 1293–1299 (1989).
Gielen et al., EMBP J 3, 835–845 (1984).
Goldberg L. and Margalit J., Mosq. News 37, 355–358 (1977).
Gordon-Kamm et al., The Plant Cell 2, 603 et seq. (1990).
Gould et al., Plant Physiol. 95, 426–434 (1991).
Hoffmann et al., Proc. Natl. Acad. Sci. USA 85, 7844–7848 (1988).
Höfte et al., Eur. J. Biochem 161, 273–280 (1986).
Höfte H. and Whiteley H. R., Microbiological Reviews 53, 242–255 (1989).
Joshi, (1987) Nucl. Acids Res. 15, 6643–6653.
Krieg et al., Z. Ang. Ent 96, 500–508 (1983).
Luthe and Quatrano, Plant and Physiology 65, 305 (1980).
Mc Pherson et al., Bio/Technology 6, 61–66 (1988).
Meeusen and Warren, Ann. Rev. Entomol. 34, 373–381 (1989).
Miller et al., Molecular and Cellular Biology 9, 5340–5349 (1989).
"The Molecular Biology of the Cell, Second Edition", Eds. Alberts et al., Garland Publishing Co., N.Y. and London (1989).
Neumann et al., Biotechniques 5, 144 (1987).
Odell et al., Nature 313, 810–812 (1985).
Schnepf et al., J. Biol. Chem. 260, 6264–6272 (1985).
Vaeck et al., Nature 327, 33–37 (1987).
Velten and Schell, Nucleic Acids Research 13, 6981–6998 (1985).
Velten et al., EMBO J 3, 2723–2730 (1984).
Widner and Whiteley, J. Bacterial 171, 965–974 (1989).
Yanisch-Perron et al., Gene 33, 103–109 (1985).

We claim:

1. A process for modifying a Bt ICP gene for expression in plant cells comprising:

1) identifying the first region of about 300 bp downstream from the translation initiation site of the coding sequence of said Bt ICP gene having a transcriptional activity which is less than 25% of the transcriptional activity of a region of similar length at the translation initiation site of said gene, and which specifically binds to nuclear proteins isolated from said plant cells in vitro; and 2) modifying about 3 to about 63 codons in said region by changing A or T nucleotides to G or C nucleotides without affecting the encoded amino acid sequence, and wherein transcription of said Bt ICP gene is increased in said plant cells.

2. A modified Bt ICP gene for expression in plant cells obtained by the process of claim 1.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GAUCACGCGA AUU  13

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

AAUUCCGGGG AUCAAUU  17

( 2 ) INFORMATION FOR SEQ ID NO:3:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CGUCGACCUG CAGCCAAGCU UGCUGA  26

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

UUGAUUGACC GGAUCCGGCU CUAGAAUU  28

( 2 ) INFORMATION FOR SEQ ID NO:5:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CGGUACCC                                                                                                         8

(2) INFORMATION FOR SEQ ID NO:6:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

AAAACCATGG CT                                                                                                   12

(2) INFORMATION FOR SEQ ID NO:7:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GTACCAAAAC CATGGCTATC GAGACCGGTT ACACCCCAAT CGATATCG                                                             48

(2) INFORMATION FOR SEQ ID NO:8:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

ATCGATTGGG GTGTAACCGG TCTCGATAGC CATGGTTTTG GTACCGAT                                                             48

(2) INFORMATION FOR SEQ ID NO:9:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

ATCGGTACCA AAACCATGGC TATCGAGACC GGTTACACCC CAATCGAT                                                             48

(2) INFORMATION FOR SEQ ID NO:10:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 16..51

(xi) SEQUENCE DESCRIPTION: SEQ ID NO:10:

ATCGGTACCA AAACC ATG GCT ATC GAG ACC GGT TAC ACC CCA ATC GAT ATC                                                 51

```
    Met  Ala  Ile  Glu  Thr  Gly  Tyr  Thr  Pro  Ile  Asp  Ile
     1              5                        10
```

G                                                                                                                      52

(2) INFORMATION FOR SEQ ID NO:11:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GATCCTCTAG AGACTGGATC AGGTACAACC AGTTCAGGAG GGAGTTAACC CTAACCGTGT     60

TAGAC                                                                65

(2) INFORMATION FOR SEQ ID NO:12:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

ATCGTGTCCC TATTCCCGAA CTACGACAGC AGGACGTACC CAATCCGAAC CGTGTCCCAG     60

TTAACCAGGG A                                                         71

(2) INFORMATION FOR SEQ ID NO:13:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GATCTACACC AACCCAGTGT TAGAGAACTT CGACGGTAGC TTCCGAGGCT CGGCTCAGGG     60

CATCG                                                                65

(2) INFORMATION FOR SEQ ID NO:14:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

AGGGAAGCAT CAGGAGCCCA CACTTGATGG ACATCCTTAA CAGCATCACC ATCTACACGG     60

ACGCT                                                                65

(2) INFORMATION FOR SEQ ID NO:15:

(i) SEQUENCE CHARACTERISTICS:
        (A) LENGTH: 73 base pairs
        (B) TYPE: nucleic acid
        (C) STRANDEDNESS: single (D) TOPOLOGY: linear (i i) MOLECULE TYPE: DNA (genomic)

(x i) SEQUENCE DESCRIPTION: SEQ ID NO:15:

```
CACAGGGGAG AGTACTACTG GTCCGGGCAC CAGATCATGG CTTCCCCTGT GGGGTTCTCG      60
GGGCCAGAAT TCG                                                         73
```

(2) INFORMATION FOR SEQ ID NO:16:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:16:

```
GATCCGAATT CTGGCCCCGA GAACCCCACA GGGGAAGCCA TGATCTGGTG CCCGGACCAG      60
TAGTAC                                                                 66
```

(2) INFORMATION FOR SEQ ID NO:17:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:17:

```
TCTCCCCTGT GAGCGTCCGT GTAGATGGTG ATGCTGTTAA GGATGTCCAT CAAGTGTGGG      60
CTCCT                                                                  65
```

(2) INFORMATION FOR SEQ ID NO:18:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:18:

```
GATGCTTCCC TCGATGCCCT GAGCCGAGCC TCGGAAGCTA CCGTCGAAGT TCTCTAACAC      60
TGGG                                                                   64
```

(2) INFORMATION FOR SEQ ID NO:19:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:19:

```
TTGGTGTAGA TCTCCCTGGT TAACTGGGAC ACGGTTCGGA TTGGGTACGT CCTGCTGTCG      60
TAGTTCGGGA A                                                           71
```

(2) INFORMATION FOR SEQ ID NO:20:

(i) SEQUENCE CHARACTERISTICS:
      (A) LENGTH: 73 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:20:

TAGGGACACG ATGTCTAACA CGGTTAGGGT TAACTCCCTC CTGAACTGGT TGTACCTGAT    60

CCAGTCTCTA GAG    73

(2) INFORMATION FOR SEQ ID NO:21:

(i) SEQUENCE CHARACTERISTICS:
      (A) LENGTH: 343 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 3..341

(xi) SEQUENCE DESCRIPTION: SEQ ID NO:21:

| GA | TCC | TCT | AGA | GAC | TGG | ATC | AGG | TAC | AAC | CAG | TTC | AGG | AGG | GAG | TTA | 47 |
|    | Ser | Ser | Arg | Asp | Trp | Ile | Arg | Tyr | Asn | Gln | Phe | Arg | Arg | Glu | Leu |    |
|    | 1   |     |     |     | 5   |     |     |     |     | 10  |     |     |     |     | 15  |    |

ACC CTA ACC GTG TTA GAC ATC GTG TCC CTA TTC CCG AAC TAC GAC AGC    95
Thr Leu Thr Val Leu Asp Ile Val Ser Leu Phe Pro Asn Tyr Asp Ser
            20              25                      30

AGG ACG TAC CCA ATC CGA ACC GTG TCC CAG TTA ACC AGG GAG ATC TAC    143
Arg Thr Tyr Pro Ile Arg Thr Val Ser Gln Leu Thr Arg Glu Ile Tyr
                35              40              45

ACC AAC CCA GTG TTA GAG AAC TTC GAC GGT AGC TTC CGA GGC TCG GCT    191
Thr Asn Pro Val Leu Glu Asn Phe Asp Gly Ser Phe Arg Gly Ser Ala
            50              55              60

CAG GGC ATC GAG GGA AGC ATC AGG AGC CCA CAC TTG ATG GAC ATC CTT    239
Gln Gly Ile Glu Gly Ser Ile Arg Ser Pro His Leu Met Asp Ile Leu
    65              70              75

AAC AGC ATC ACC ATC TAC ACG GAC GCT CAC AGG GGA GAG TAC TAC TGG    287
Asn Ser Ile Thr Ile Tyr Thr Asp Ala His Arg Gly Glu Tyr Tyr Trp
80              85              90              95

TCC GGG CAC CAG ATC ATG GCT TCC CCT GTG GGG TTC TCG GGG CCA GAA    335
Ser Gly His Gln Ile Met Ala Ser Pro Val Gly Phe Ser Gly Pro Glu
            100             105             110

TTC GGA TC    343
Phe Gly (2) INFORMATION FOR SEQ ID NO:22:

(i) SEQUENCE CHARACTERISTICS:
      (A) LENGTH: 3201 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: misc_feature
      (B) LOCATION: 2151..2155
      (D) OTHER INFORMATION: /note= "Nucleotides 2151-2155
            wherein N is not known."

( x i ) SEQUENCE DESCRIPTION: SEQ ID NO:22:

| | | | | | | |
|---|---|---|---|---|---|---|
| AAATGGATAA | ATAGCCTTGC | TTCCTATTAT | ATCTTCCCAA | ATTACCAATA | CATTACACTA | 60 |
| GCATCTGAAT | TTCATAACCA | ATCTCGATAC | ACCAAATCGA | TGGATCCCGA | TAACAATCCG | 120 |
| AACATCAATG | AATGCATTCC | TTATAATTGT | TTAAGTAACC | CTGAAGTAGA | AGTATTAGGT | 180 |
| GGAGAAAGAA | TAGAAACTGG | TTACACCCCA | ATCGATATTT | CCTTGTCGCT | AACGCAATTT | 240 |
| CTTTTGAGTG | AATTTGTTCC | CGGTGCTGGA | TTTGTGTTAG | GACTAGTTGA | TATAATATGG | 300 |
| GGAATTTTTG | GTCCCTCTCA | ATGGGACGCA | TTTCTTGTAC | AAATTGAACA | GTTAATTAAC | 360 |
| CAAAGAATAG | AAGAATTCGC | TAGGAACCAA | GCCATTTCTA | GATTAGAAGG | ACTAAGCAAT | 420 |
| CTTTATCAAA | TTTACGCAGA | ATCTTTTAGA | GAGTGGGAAG | CAGATCCTAC | TAATCCAGCA | 480 |
| TTAAGAGAAG | AGATGCGTAT | TCAATTCAAT | GACATGAACA | GTGCCCTTAC | AACCGCTATT | 540 |
| CCTCTTTTTG | CAGTTCAAAA | TTATCAAGTT | CCTCTTTTAT | CAGTATATGT | TCAAGCTGCA | 600 |
| AATTTACATT | TATCAGTTTT | GAGAGATGTT | TCAGTGTTTG | GACAAAGGTG | GGGATTTGAT | 660 |
| GCCGCGACTA | TCAATAGTCG | TTATAATGAT | TTAACTAGGC | TTATTGGCAA | CTATACAGAT | 720 |
| CATGCTGTAC | GCTGGTACAA | TACGGGATTA | GAGCGTGTAT | GGGGACCGGA | TTCTAGAGAT | 780 |
| TGGATAAGAT | ATAATCAATT | TAGAAGAGAA | TTAACACTAA | CTGTATTAGA | TATCGTTTCT | 840 |
| CTATTTCCGA | ACTATGATAG | TAGAACGTAT | CCAATTCGAA | CAGTTTCCCA | ATTAACAAGA | 900 |
| GAAATTTATA | CAAACCCAGT | ATTAGAAAAT | TTTGATGGTA | GTTTTCGAGG | CTCGGCTCAG | 960 |
| GGCATAGAAG | GAAGTATTAG | GAGTCCACAT | TTGATGGATA | TACTTAACAG | TATAACCATC | 1020 |
| TATACGGATG | CTCATAGAGG | AGAATATTAT | TGGTCAGGGC | ATCAAATAAT | GGCTTCTCCT | 1080 |
| GTAGGGTTTT | CGGGGCCAGA | ATTCACTTTT | CCGCTATATG | GAACTATGGG | AAATGCAGCT | 1140 |
| CCACAACAAC | GTATTGTTGC | TCAACTAGGT | CAGGGCGTGT | ATAGAACATT | ATCGTCCACT | 1200 |
| TTATATAGAA | GACCTTTTAA | TATAGGGATA | AATAATCAAC | AACTATCTGT | TCTTGACGGG | 1260 |
| ACAGAATTTG | CTTATGGAAC | CTCCTCAAAT | TTGCCATCCG | CTGTATACAG | AAAAAGCGGA | 1320 |
| ACGGTAGATT | CGCTGGATGA | AATACCGCCA | CAGAATAACA | ACGTGCCACC | TAGGCAAGGA | 1380 |
| TTTAGTCATC | GATTAAGCCA | TGTTTCAATG | TTTCGTTCAG | GCTTTAGTAA | TAGTAGTGTA | 1440 |
| AGTATAATAA | GAGCTCCTAT | GTTCTCTTGG | ATACATCGTA | GTGCTGAATT | TAATAATATA | 1500 |
| ATTCCTTCAT | CACAAATTAC | ACAAATACCT | TTAACAAAAT | CTACTAATCT | TGGCTCTGGA | 1560 |
| ACTTCTGTCG | TTAAAGGACC | AGGATTTACA | GGAGGAGATA | TTCTTCGAAG | AACTTCACCT | 1620 |
| GGCCAGATTT | CAACCTTAAG | AGTAAATATT | ACTGCACCAT | TATCACAAAG | ATATCGGGTA | 1680 |
| AGAATTCGCT | ACGCTTCTAC | CACAAATTTA | CAATTCCATA | CATCAATTGA | CGGAAGACCT | 1740 |
| ATTAATCAGG | GGAATTTTTC | AGCAACTATG | AGTAGTGGGA | GTAATTTACA | GTCCGGAAGC | 1800 |
| TTTAGGACTG | TAGGTTTTAC | TACTCCGTTT | AACTTTTCAA | ATGGATCAAG | TGTATTTACG | 1860 |
| TTAAGTGCTC | ATGTCTTCAA | TTCAGGCAAT | GAAGTTTATA | TAGATCGAAT | TGAATTTGTT | 1920 |
| CCGGCAGAAG | TAACCTTTGA | GGCAGAATAT | GATTTAGAAA | GAGCACAAAA | GGCGGTGAAT | 1980 |
| GAGCTGTTTA | CTTCTTCCAA | TCAAATCGGG | TTAAAAACAG | ATGTGACGGA | TTATCATATT | 2040 |
| GATCAAGTAT | CCAATTTAGT | TGAGTGTTTA | TCTGATGAAT | TTTGTCTGGA | TGAAAAAAAA | 2100 |
| GAATTGTCCG | AGAAAGTCAA | ACATGCGAAG | CGACTTAGTG | ATGAGCGGAA | NNNNCCTCG | 2160 |
| AGCTTGGATG | GATTGCACGC | AGGTTCTCCG | GCCGCTTGGG | TGGAGAGGCT | ATTCGGCTAT | 2220 |
| GACTGGGCAC | AACAGACAAT | CGGCTGCTCT | GATGCCGCCG | TGTTCCGGCT | GTCAGCGCAG | 2280 |
| GGGCGCCCGG | TTCTTTTTGT | CAAGACCGAC | CTGTCCGGTG | CCCTGAATGA | ACTGCAGGAC | 2340 |

| | | | | | | |
|---|---|---|---|---|---|---|
| GAGGCAGCGC | GGCTATCGTG | GCTGGCCACG | ACGGGCGTTC | CTTGCGCAGC | TGTGCTCGAC | 2400 |
| GTTGTCACTG | AAGCGGGAAG | GGACTGGCTG | CTATTGGGCG | AAGTGCCGGG | GCAGGATCTC | 2460 |
| CTGTCATCTC | ACCTTGCTCC | TGCCGAGAAA | GTATCCATCA | TGGCTGATGC | AATGCGGCGG | 2520 |
| CTGCATACGC | TTGATCCGGC | TACCTGCCCA | TTCGACCACC | AAGCGAAACA | TCGCATCGAG | 2580 |
| CGAGCACGTA | CTCGGATGGA | AGCCGGTCTT | GTCGATCAGG | ATGATCTGGA | CGAAGAGCAT | 2640 |
| CAGGGGCTCG | CGCCAGCCGA | ACTGTTCGCC | AGGCTCAAGG | CGCGCATGCC | CGACGGCGAG | 2700 |
| GATCTCGTCG | TGACCCATGG | CGATGCCTGC | TTGCCGAATA | TCATGGTGGA | AAATGGCCGC | 2760 |
| TTTTCTGGAT | TCATCGACTG | TGGCCGGCTG | GGTGTGGCGG | ACCGCTATCA | GGACATAGCG | 2820 |
| TTGGCTACCC | GTGATATTGC | TGAAGAGCTT | GGCGGCGAAT | GGGCTGACCG | CTTCCTCGTG | 2880 |
| CTTTACGGTA | TCGCCGCTCC | CGATTCGCAG | CGCATCGCCT | TCTATCGCCT | TCTTGACGAG | 2940 |
| TTCTTCTGAC | AGATCCCCCG | ATGAGCTAAG | CTAGCTATAT | CATCAATTTA | TGTATTACAC | 3000 |
| ATAATATCGC | ACTCAGTCTT | TCATCTACGG | CAATGTACCA | GCTGATATAA | TCAGTTATTG | 3060 |
| AAATATTTCT | GAATTTAAAC | TTGCATCAAT | AAATTTATGT | TTTTGCTTGG | ACTATAATAC | 3120 |
| CTGACTTGTT | ATTTTATCAA | TAAATATTTA | AACTATATTT | CTTTCAAGAT | GGGAATTAAC | 3180 |
| ATCTACAAAT | TGCCTTTTCT | T | | | | 3201 |

( 2 ) INFORMATION FOR SEQ ID NO:23:

( i ) SEQUENCE CHARACTERISTICS:
        ( A ) LENGTH: 3200 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 2078..2082
        ( D ) OTHER INFORMATION: /note= "Nucleotides 2078-2082
            wherein N is not known."

( x i ) SEQUENCE DESCRIPTION: SEQ ID NO:23:

| | | | | | | |
|---|---|---|---|---|---|---|
| AAATGGATAA | ATAGCCTTGC | TTCCTATTAT | ATCTTCCCAA | ATTACCAATA | CATTACACTA | 60 |
| GCATCTGAAT | TTCATAACCA | ATCTCGATAC | ACCAAATCGG | TACCAAAACC | ATGGCTATCG | 120 |
| AGACCGGTTA | CACCCCAATC | GATATTTCCT | TGTCGCTAAC | GCAATTTCTT | TTGAGTGAAT | 180 |
| TTGTTCCCGG | TGCTGGATTT | GTGTTAGGAC | TAGTTGATAT | AATATGGGGA | ATTTTTGGTC | 240 |
| CCTCTCAATG | GGACGCATTT | CTTGTACAAA | TTGAACAGTT | AATTAACCAA | AGAATAGAAG | 300 |
| AATTCGCTAG | GAACCAAGCC | ATTTCTAGAT | TAGAAGGACT | AAGCAATCTT | TATCAAATTT | 360 |
| ACGCAGAATC | TTTTAGAGAG | TGGGAAGCAG | ATCCTACTAA | TCCAGCATTA | AGAGAAGAGA | 420 |
| TGCGTATTCA | ATTCAATGAC | ATGAACAGTG | CCCTTACAAC | CGCTATTCCT | CTTTTTGCAG | 480 |
| TTCAAAATTA | TCAAGTTCCT | CTTTTATCAG | TATATGTTCA | AGCTGCAAAT | TTACATTTAT | 540 |
| CAGTTTTGAG | AGATGTTTCA | GTGTTTGGAC | AAAGGTGGGG | ATTTGATGCC | GCGACTATCA | 600 |
| ATAGTCGTTA | TAATGATTTA | ACTAGGCTTA | TTGGCAACTA | TACAGATCAT | GCTGTACGCT | 660 |
| GGTACAATAC | GGGATTAGAG | CGTGTATGGG | GACCGGATTC | TAGAGACTGG | ATCAGGTACA | 720 |
| ACCAGTTCAG | GAGGGAGTTA | ACCCTAACCG | TGTTAGACAT | CGTGTCCCTA | TTCCCGAACT | 780 |
| ACGACAGCAG | GACGTACCCA | ATCCGAACCG | TGTCCAGTT | AACCAGGGAG | ATCTACACCA | 840 |
| ACCCAGTGTT | AGAGAACTTC | GACGGTAGCT | TCCGAGGCTC | GGCTCAGGGC | ATCGAGGGAA | 900 |
| GCATCAGGAG | CCCACACTTG | ATGGACATCC | TTAACAGCAT | CACCATCTAC | ACGGACGCTC | 960 |

```
ACAGGGGAGA  GTACTACTGG  TCCGGGCACC  AGATCATGGC  TTCCCCTGTG  GGGTTCTCGG  1020
GGCCAGAATT  CACTTTTCCG  CTATATGGAA  CTATGGGAAA  TGCAGCTCCA  CAACAACGTA  1080
TTGTTGCTCA  ACTAGGTCAG  GGCGTGTATA  GAACATTATC  GTCCACTTTA  TATAGAAGAC  1140
CTTTTAATAT  AGGGATAAAT  AATCAACAAC  TATCTGTTCT  TGACGGGACA  GAATTTGCTT  1200
ATGGAACCTC  CTCAAATTTG  CCATCCGCTG  TATACAGAAA  AAGCGGAACG  GTAGATTCGC  1260
TGGATGAAAT  ACCGCCACAG  AATAACAACG  TGCCACCTAG  GCAAGGATTT  AGTCATCGAT  1320
TAAGCCATGT  TTCAATGTTT  CGTTCAGGCT  TTAGTAATAG  TAGTGTAAGT  ATAATAAGAG  1380
CTCCTATGTT  CTCTTGGATA  CATCGTAGTG  CTGAATTTAA  TAATATAATT  CCTTCATCAC  1440
AAATTACACA  AATACCTTTA  ACAAATCTA   CTAATCTTGG  CTCTGGAACT  TCTGTCGTTA  1500
AAGGACCAGG  ATTTACAGGA  GGAGATATTC  TTCGAAGAAC  TTCACCTGGC  CAGATTTCAA  1560
CCTTAAGAGT  AAATATTACT  GCACCATTAT  CACAAAGATA  TCGGGTAAGA  ATTCGCTACG  1620
CTTCTACCAC  AAATTTACAA  TTCCATACAT  CAATTGACGG  AAGACCTATT  AATCAGGGA   1680
ATTTTTCAGC  AACTATGAGT  AGTGGGAGTA  ATTTACAGTC  CGGAAGCTTT  AGGACTGTAG  1740
GTTTTACTAC  TCCGTTTAAC  TTTTCAAATG  GATCAAGTGT  ATTTACGTTA  AGTGCTCATG  1800
TCTTCAATTC  AGGCAATGAA  GTTTATATAG  ATCGAATTGA  ATTTGTTCCG  GCAGAAGTAA  1860
CCTTTGAGGC  AGAATATGAT  TTAGAAAGAG  CACAAAAGGC  GGTGAATGAG  CTGTTTACTT  1920
CTTCCAATCA  AATCGGGTTA  AAAACAGATG  TGACGGATTA  TCATATTGAT  CAAGTATCCA  1980
ATTTAGTTGA  GTGTTTATCT  GATGAATTTT  GTCTGGATGA  AAAAAAAGAA  TTGTCCGAGA  2040
AAGTCAAACA  TGCGAAGCGA  CTTAGTGATG  AGCGGAANNN  NNCCTCGAGC  TTGGATGGAT  2100
TGCACGCAGG  TTCTCCGGCC  GCTTGGGTGG  AGAGGCTATT  CGGCTATGAC  TGGGCACAAC  2160
AGACAATCGG  CTGCTCTGAT  GCCGCCGTGT  TCCGGCTGTC  AGCGCAGGGG  CGCCCGGTTC  2220
TTTTTGTCAA  GACCGACCTG  TCCGGTGCCC  TGAATGAACT  GCAGGACGAG  GCAGCGCGGC  2280
TATCGTGGCT  GGCCACGACG  GGCGTTCCTT  GCGCAGCTGT  GCTCGACGTT  GTCACTGAAG  2340
CGGGAAGGGA  CTGGCTGCTA  TTGGGCGAAG  TGCCGGGGCA  GGATCTCCTG  TCATCTCACC  2400
TTGCTCCTGC  CGAGAAAGTA  TCCATCATGG  CTGATGCAAT  GCGGCGGCTG  CATACGCTTG  2460
ATCCGGCTAC  CTGCCCATTC  GACCACCAAG  CGAAACATCG  CATCGAGCGA  GCACGTACTC  2520
GGATGGAAGC  CGGTCTTGTC  GATCAGGATG  ATCTGGACGA  AGAGCATCAG  GGGCTCGCGC  2580
CAGCCGAACT  GTTCGCCAGG  CTCAAGGCGC  GCATGCCCGA  CGGCGAGGAT  CTCGTCGTGA  2640
CCCATGGCGA  TGCCTGCTTG  CCGAATATCA  TGGTGGAAAA  TGGCCGCTTT  TCTGGATTCA  2700
TCGACTGTGG  CCGGCTGGGT  GTGGCGGACC  GCTATCAGGA  CATAGCGTTG  GCTACCCGTG  2760
ATATTGCTGA  AGAGCTTGGC  GGCGAATGGG  CTGACCGCTT  CCTCGTGCTT  TACGGTATCG  2820
CCGCTCCCGA  TTCGCAGCGC  ATCGCCTTCT  ATCGCCTTCT  TGACGAGTTC  TTCTGACAGA  2880
TCCCCCGATG  AGCTAAGCTA  GCTATATCAT  CAATTTATGT  ATTACACATA  ATATCGCACT  2940
CAGTCTTTCA  TCTACGGCAA  TGTACCAGCT  GATATAATCA  GTTATTGAAA  TATTTCTGAA  3000
TTTAAACTTG  CATCAATAAA  TTTATGTTTT  TGCTTGGACT  ATAATACCTG  ACTTGTTATT  3060
TTATCAATAA  ATATTTAAAC  TATATTTCTT  TCAAGATGGG  AATTAACATC  TACAAATTGC  3120
CTTTTCTTAT  CGACCATGTA  CGGGTACCGA  GCTCGAATTC  CACGCAGCAG  GTCTCATCAA  3180
GACGATCTAC  CCGAGTAACA                                                  3200
```